US008609143B2

(12) United States Patent
Fischer et al.

(10) Patent No.: US 8,609,143 B2
(45) Date of Patent: Dec. 17, 2013

(54) MORPHINE POLYMER RELEASE SYSTEM

(75) Inventors: Gina Fischer, Værløse (DK); Daniel Bar-Shalom, Kokkedal (DK); Lillian Slot, Virum (DK); Christine Andersen, Vedbæk (DK)

(73) Assignee: Egalet Ltd., London (GB)

( * ) Notice: Subject to any disclaimer, the term of this patent is extended or adjusted under 35 U.S.C. 154(b) by 914 days.

(21) Appl. No.: 12/078,312

(22) Filed: Mar. 28, 2008

(65) Prior Publication Data
US 2008/0254123 A1 Oct. 16, 2008

Related U.S. Application Data

(63) Continuation of application No. 10/490,169, filed as application No. PCT/DK02/00619 on Sep. 23, 2002, now abandoned.

(30) Foreign Application Priority Data

Sep. 21, 2001 (DK) .................................. 2001 01376

(51) Int. Cl.
A61K 9/14 (2006.01)

(52) U.S. Cl.
USPC ............ 424/486; 424/484; 424/408; 424/409

(58) Field of Classification Search
USPC .................................. 424/486, 484
See application file for complete search history.

(56) References Cited

U.S. PATENT DOCUMENTS

| 3,835,221 A | 9/1974 | Fulberth et al. |
| 4,330,338 A | 5/1982 | Banker |
| 4,389,393 A | 6/1983 | Schor et al. |
| 4,503,067 A | 3/1985 | Wiedemann et al. |
| 4,824,675 A | 4/1989 | Wong et al. |
| 4,844,984 A | 7/1989 | Eckenhoff et al. |
| 4,873,080 A | 10/1989 | Brickl et al. |
| 4,892,742 A | 1/1990 | Shah |
| 4,898,733 A | 2/1990 | DePrince et al. |
| 5,068,112 A | 11/1991 | Samejima et al. |
| 5,102,668 A | 4/1992 | Eichel et al. |
| 5,213,808 A | 5/1993 | Bar-Shalom et al. |
| 5,419,917 A | 5/1995 | Chen et al. |
| 5,422,123 A | 6/1995 | Conte et al. |
| 5,478,577 A | 12/1995 | Sackler et al. |
| 5,593,695 A * | 1/1997 | Merrill et al. ................. 424/480 |
| 5,618,560 A | 4/1997 | Bar-Shalom et al. |
| 5,741,524 A | 4/1998 | Staniforth et al. |
| 5,952,005 A | 9/1999 | Olsson et al. |
| 6,183,778 B1 | 2/2001 | Conte et al. |
| 6,245,357 B1 | 6/2001 | Edgren et al. |
| 6,267,981 B1 | 7/2001 | Okamoto et al. |
| 6,267,985 B1 | 7/2001 | Chen et al. |
| 6,383,471 B1 | 5/2002 | Chen et al. |
| 6,395,299 B1 | 5/2002 | Babich et al. |
| 6,458,824 B1 | 10/2002 | Iwata et al. |
| 6,488,962 B1 | 12/2002 | Berner et al. |
| 6,517,866 B1 | 2/2003 | Am Ende et al. |
| 6,534,085 B1 | 3/2003 | Zeligs |
| 6,562,375 B1 | 5/2003 | Sako et al. |
| 6,632,832 B1 | 10/2003 | Burman et al. |
| 6,709,678 B2 | 3/2004 | Gruber |
| 6,730,326 B2 | 5/2004 | Beyer et al. |
| 6,787,156 B1 | 9/2004 | Bar-Shalom |
| 7,883,722 B2 | 2/2011 | Bar-Shalom |
| 2001/0036959 A1 | 11/2001 | Gabel et al. |
| 2001/0036960 A1 | 11/2001 | Decker et al. |
| 2001/0053791 A1 | 12/2001 | Babcock et al. |
| 2002/0054911 A1 | 5/2002 | Oh |
| 2003/0035836 A1 | 2/2003 | Shanghvi et al. |
| 2003/0203055 A1 | 10/2003 | Rao et al. |
| 2004/0028733 A1 | 2/2004 | Tracy et al. |
| 2004/0151772 A1 | 8/2004 | Andersen et al. |
| 2004/0213849 A1 | 10/2004 | Sowden et al. |
| 2004/0234602 A1 | 11/2004 | Fischer et al. |
| 2004/0253310 A1 | 12/2004 | Fischer et al. |
| 2005/0019399 A1 | 1/2005 | Fischer et al. |
| 2005/0019405 A1 | 1/2005 | Bar-Shalom |
| 2005/0089569 A1 | 4/2005 | Bar-Shalom |
| 2005/0163837 A1 | 7/2005 | Boehm et al. |
| 2007/0003617 A1 | 1/2007 | Fischer et al. |
| 2007/0042044 A1 | 2/2007 | Fischer et al. |
| 2008/0234352 A1 | 9/2008 | Fischer et al. |

(Continued)

FOREIGN PATENT DOCUMENTS

| DE | 2415490 A1 | 10/1974 |
| DE | 2332484 C2 | 11/1984 |

(Continued)

OTHER PUBLICATIONS

Hoffman et al. "Phase Diagrams and Aggregation Behavior of Poly (oxyethylene)-Poly (oxypropylene)-Poly(oxyethylene) Triblock Copolymers in Aqueous Solutions", 1994, Macromolecules, 27, pp. 4145-4159.*

Packer et al. "Molecular Aspects of a-Tocotrienol Antioxidant Action and Cell Signaling", 2001, Journal of Nutrition, vol. 131, No. 2, pp. 369S-373S.*

U.S. Appl. No. 11/915,655, filed Nov. 27, 2007, Bar-Shalom et al.

Bravo et al., "In-vitro studies of diclofenac sodium controlled-release from biopolymeric hydrophilic matrices," *J. Pharmaceutical Science*, vol. 5, No. 3, pp. 213-219 (2002).

The Condensed Chemical Dictionary, "mixture," 9th edition, p. 584 (1977).

Giunchedi et al., "Hydrophilic matrices for the extended release of a model drug exhibiting pH-dependent solubility," *International Journal of Pharmaceutics*, vol. 85, pp. 141-147 (1992).

Hoshi et al., Cellulose and its Derivatives, pp. 24-25 (1992).

Miyazaki et al., "In situ-gelling gellan formulations as vehicles for oral drug delivery," *J. Control Release*, vol. 60, pp. 287-295 (1999).

(Continued)

Primary Examiner — James Rogers
(74) Attorney, Agent, or Firm — Foley & Lardner LLP

(57) ABSTRACT

A pharmaceutical composition for controlled release of an active substance is provided. The active substance is released into an aqueous medium by erosion of at least one surface of the composition. The composition comprises i) a matrix comprising a) polymer or a mixture of polymers, b) an active substance and, optionally, c) one or more pharmaceutically acceptable excipients, and ii) a coating.

38 Claims, 6 Drawing Sheets

(56) References Cited

U.S. PATENT DOCUMENTS

| | | | |
|---|---|---|---|
| 2008/0254122 | A1 | 10/2008 | Fischer et al. |
| 2008/0254124 | A1 | 10/2008 | Bar-Shalom |
| 2008/0268057 | A1 | 10/2008 | Andersen et al. |
| 2009/0274759 | A1 | 11/2009 | Bar-Shalom et al. |

FOREIGN PATENT DOCUMENTS

| | | |
|---|---|---|
| EP | 0 908 181 | 4/1999 |
| EP | 1 027 888 A2 | 8/2000 |
| EP | 0 335 560 | 1/2002 |
| EP | 1 371 360 | 5/2005 |
| GB | 1430684 | 3/1976 |
| GB | 2170104 | 7/1986 |
| GB | 2182559 | 5/1987 |
| JP | 60/255719 | 12/1985 |
| JP | 07/100191 | 4/1995 |
| WO | WO 86/04817 | 8/1986 |
| WO | WO-89/09066 A | 10/1989 |
| WO | WO 90/08536 | 8/1990 |
| WO | WO-91/04015 | 4/1991 |
| WO | WO-91/04015 A | 4/1991 |
| WO | WO 92/09270 | 6/1992 |
| WO | WO-95/22962 A | 8/1995 |
| WO | WO-99/44591 A | 9/1999 |
| WO | WO-99/51208 A | 10/1999 |
| WO | WO 01/35958 | 5/2001 |
| WO | WO 01/51035 | 7/2001 |
| WO | WO 01/51036 | 7/2001 |
| WO | WO 01/74357 | 10/2001 |
| WO | WO 02/065834 | 8/2002 |
| WO | WO 02/092078 | 11/2002 |
| WO | WO 03/039521 A1 | 5/2003 |
| WO | WO 2005/007074 | 1/2005 |
| WO | WO 2005/027878 | 3/2005 |

OTHER PUBLICATIONS

Rowe et al., "Glycerin," *Handbook of Pharmaceutical Excipients*, Pharmaceutical Presse, 4th edition, pp. 257-258 (2003).

www.wikipedia.org, web page on phosphoric acid, http://en.wikipedia.org/wiki/Phosphoric_acid, May 8, 2007.

Yamakita et al., "In Vitro/in Vivo Evaluation of Two Series of TA5707F Controlled Release Matrix Tablets Prepared with Hydroxypropyl Methyl Cellulose Derivatives with Entero-Soluble or Gel-Formation Properties," *Biol. Pharm. Bull*, vol. 18, No. 10, pp. 1409-1416 (1995).

Office Action issued Oct. 24, 2006 by the Examiner in U.S. Appl. No. 10/703,084 (US 2004/0151772).

Office Action issued Jun. 14, 2007 by the Examiner in U.S. Appl. No. 10/703,084 (US 2004/0151772).

Office Action issued Dec. 20, 2007 by the Examiner in U.S. Appl. No. 10/827,521 (US 2005/0019405).

Office Action issued Jul. 25, 2006 by the Examiner in U.S. Appl. No. 10/490,308 (US 2004/0234602).

Office Action issued Mar. 9, 2007 by the Examiner in U.S. Appl. No. 10/490,308 (US 2004/0234602).

Office Action issued Oct. 3, 2006 by the Examiner in U.S. Appl. No. 10/490,170 (US 2005/0019399).

Office Action issued May 9, 2007 by the Examiner in U.S. Appl. No. 10/490,170 (US 2005/0019399).

Office Action issued May 14, 2008 by the Examiner in U.S. Appl. No. 10/845,522 (US 2005/0089569).

Office Action issued Jun. 16, 2006 by the Examiner in U.S. Appl. No. 10/845,522 (US 2005/0089569).

Office Action issued Oct. 27, 2005 by the Examiner in U.S. Appl. No. 10/845,522 (US 2005/0089569).

Office Action issued Jul. 29, 2005 by the Examiner in U.S. Appl. No. 10/845,522 (US 2005/0089569).

Office Action issued Mar. 21, 2007 by the Examiner in U.S. Appl. No. 10/845,522 (US 2005/0089569).

Office Action issued Dec. 23, 2008 by the Examiner in U.S. Appl. No. 10/550,685 (US 2007/0042044).

Office Action issued Dec. 15, 2008 by the Examiner in U.S. Appl. No. 12/213,087 (US 2008/0254124).

Office Action issued Jun. 16, 2009 by the Examiner in U.S. Appl. No. 10/550,453 (US 2007/0042044).

Office Action issued Jan. 13, 2009 by the Examiner in U.S. Appl. No. 10/845,522 (US 2005/0089569).

Office Action issued Jun. 17, 2009 by the Examiner in U.S. Appl. No. 10/550,685 (US 2007/0042044).

Office Action issued Apr. 29, 2009 by the Examiner in U.S. Appl. No. 12/076,105 (US 2008/0268057).

Office Action issued Sep. 29, 2009 by the Examiner in U.S. Appl. No. 12/076,105 (US 2008/0268057).

Office Action issued Apr. 5, 2010 by the Examiner in U.S. Appl. No. 12/076,105 (US 2008/0268057).

Office Action issued Nov. 10, 2009 by the Examiner in U.S. Appl. No. 10/550,453 (US 2007/0003617).

Office Action issued Apr. 13, 2010 by the Examiner in U.S. Appl. No. 10/550,453 (US 2007/0003617).

Office Action issued Mar. 1, 2010 by the Examiner in U.S. Appl. No. 10/550,685 (US 2007/0042044).

Office Action issued Nov. 4, 2009 by the Examiner in U.S. Appl. No. 10/845,522 (US 2005/0089569).

Marvola et al., "Enteric polymers as binders and coating materials in multiple-unit site-specific drug delivery systems," *European Journal of Pharmaceutical Sciences*, vol. 7, pp. 259-267, 1999.

Dubbs et al., "Solubility of Vitamin E ($\alpha$-Tocopherol) and Vitamin $K_3$ (Menadione) in Ethanol-Water Mixture," *J. Chem. Eng. Data*, vol. 43, pp. 590-591, 1998.

Merck Index (9th .ed.) Entry No. 9681 for Vitamin E, p. 1290, 1976.

Varshosaz et al., "Use of enteric polymers for production of microspheres by extrusion-spheronization," *Pharmaceutica Acta Helvetiae*, vol. 72, pp. 145-152. 1997.

Office Action issued on Jun. 18, 2010 by the Examiner in U.S. Appl. No. 12/076,105 (US 2008/0268057).

Office Action issued Aug. 3, 2006, in U.S. Appl. No. 10/490,169, 11 sheets.

Office Action issued Mar. 2, 2007, in U.S. Appl. No. 10/490,169, 13 sheets.

Office Action issued on Jan. 20, 2011 by the Examiner in U.S. Appl. No. 10/550,453 (US 2007/0003617).

Office Action issued on Jun. 7, 2011 by the Examiner in U.S. Appl. No. 10/550,453 (US 2007/0003617).

Office Action issued on Aug. 5, 2010 by the Examiner in U.S. Appl. No. 10/550,453 (US 2007/0003617).

Notice of Allowance issued on Oct. 6, 2010 by the Examiner in U.S. Appl. No. 10/845,522 (US 7,883,722).

Office Action issued on May 11, 2011 by the Examiner in U.S. Appl. No. 11/596,123 (US.

Office Action issued on Jun. 9, 2011 by the Examiner in U.S. Appl. No. 12/073,691 (US 2008/0234352).

Office Action issued on Apr. 28, 2011 by the Examiner in U.S. Appl. No. 12/073,691 (US 2008/0234352).

Office Action issued on Feb. 18, 2011 by the Examiner in U.S. Appl. No. 12/076,105 (US 2008/0268057).

Office Action issued on Nov. 24, 2010 by the Examiner in U.S. Appl. No. 12/076,105 (US 2008/0268057).

Office Action issued on Mar. 31, 2011 by the Examiner in U.S. Appl. No. 12/073,692 (US 2008/0254122).

Notice of Allowance issued on Feb. 11, 2013 by the Examiner in U.S. Appl. No. 12/076,105 (US2008/0268057).

Office Action issued on Dec. 6, 2012 by the Examiner in U.S. Appl. No. 12/073,692 (US2008/0254122).

Office Action issued on Oct. 11, 2011 by the Examiner in U.S. Appl. No. 12/073,692 (US 2008/0254122).

Office Action issued on Oct. 27, 2011 by the Examiner in U.S. Appl. No. 12/073,691 (US 2008/0234352).

(56) References Cited

OTHER PUBLICATIONS

Office Action issued on Jan. 31, 2012 by the Examiner in U.S. Appl. No. 12/642,416 (US 2010/0166866).
Final Office Action issued on Feb. 1, 2012 by the Examiner in U.S. Appl. No. 10/550,685 (US2007/0042044).
Notice of allowance issued on Jun. 5, 2012 by the Examiner in U.S. Appl. No. 10/550,685 (US2007/0042044).
Wikipedia, "Phosphoric Acid," http://en.wikipedia.org/wiki/Phosphoric_acid downloaded May 10, 2012.
Office Action issued on Jun. 20, 2012 by the Examiner in U.S. Appl. No. 11/915,655 (US 2009/0274759).
Office Action issued on Apr. 24, 2012 by the Examiner in U.S. Appl. No. 12/076,105 (US 2008/0268057).
Office Action issued on Jul. 10, 2012 by the Examiner in U.S. Appl. No. 12/073,692 (US 2008/0254122).

* cited by examiner

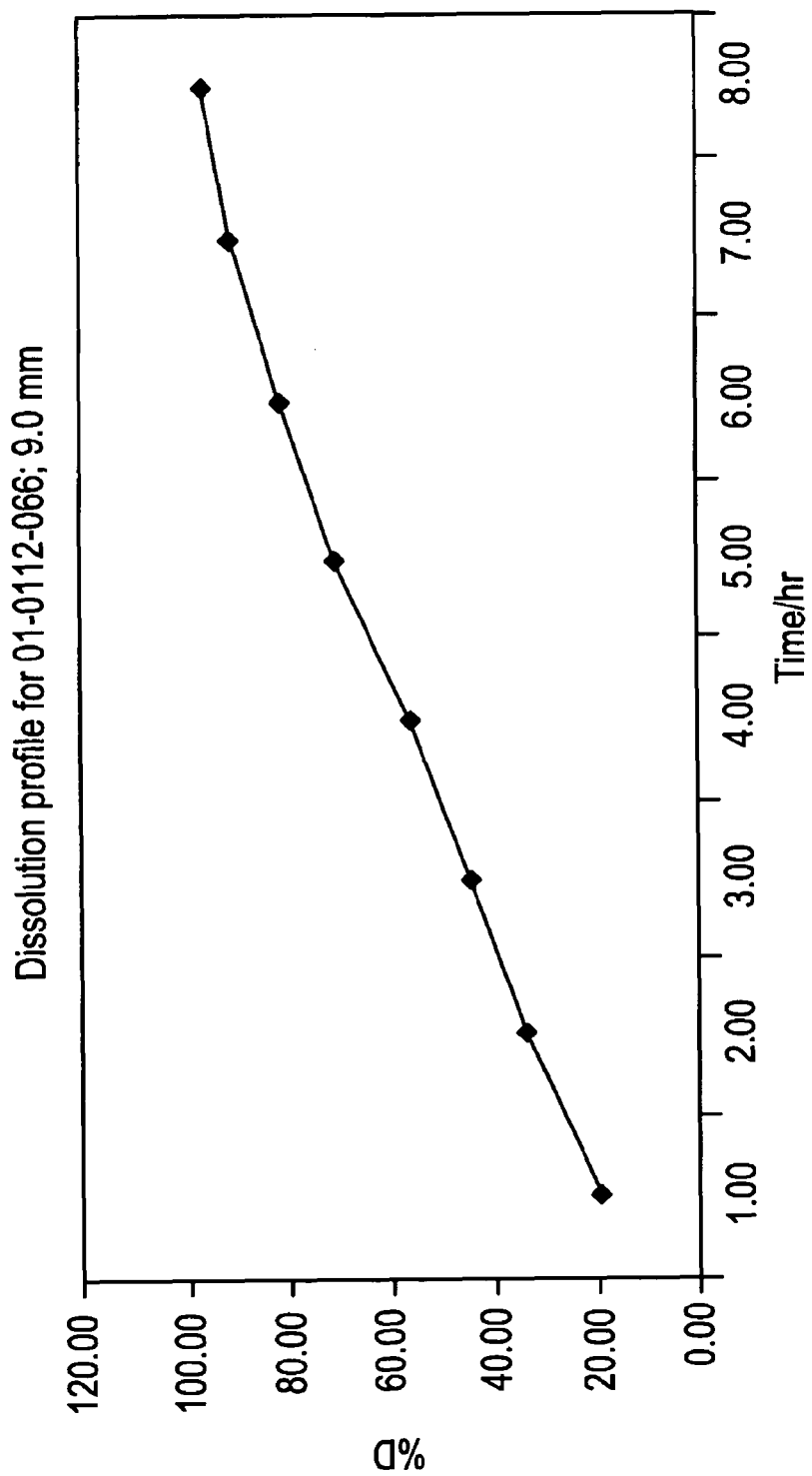

Dissolution profile for 02-0036-066

Dissolution profile for 02-0018-066

MORPHINE POLYMER RELEASE SYSTEM

FIELD OF THE INVENTION

The present invention relates to a novel pharmaceutical composition for controlled release of an opioid like e.g. morphine into an aqueous medium. The pharmaceutical composition is a coated matrix composition in which the matrix composition comprises a) a polymer or a mixture of polymers, b) an opioid like e.g. morphine and, optionally, c) one or more pharmaceutically acceptable excipients. The coating remains intact during the release phase and may thereafter crumble and/or erode. Furthermore, the coating covers the matrix composition in such a manner that only a specific surface area of the matrix composition is subject to erosion in an aqueous medium, i.e. the surface area from which the active substance is release is kept substantial constant during the time period.

The polymer mentioned under a) above may suitably be a substantially water soluble or crystalline polymer or a mixture of substantially water soluble and/or crystalline polymers The design of the pharmaceutical composition is based on the finding that it is possible to control the release from such a composition by ensuring that the release predominantly takes place by erosion. In order to ensure erosion based release a balance must be obtained between the diffusion rate of water into the matrix composition and the dissolution rate of the matrix composition.

Accordingly, the invention relates to an opioid containing pharmaceutical composition for oral use, which provides zero order release based on controlling the balance between matrix erosion rate and diffusion rate in the matrix.

The invention also provides various combinations of immediate release opioid compositions and controlled release opioid compositions.

DISCLOSURE OF THE INVENTION

The present invention relates to a controlled release composition comprising an opioid as a therapeutically, prophylactically and/or diagnostically active substance. The opioids are generally used in analgesic treatment and there is a need for developing compositions for oral use, which have a lower administration frequency. Thus once or twice daily administrations would be preferred. A controlled release composition according to the invention aim at a zero order release of the opioid in a predetermined pattern to reduce and/or delay the peak plasma concentration without affecting the extent of drug bioavailability. The frequency of undesirable side effects may be reduced and due to the delay in the time it may take to obtain the peak plasma concentration and the extension of the time at the therapeutically active plasma concentration, the frequency of the administration may be reduced to a dosage taken only twice or once daily. This also serves to improve patient compliance. A further advantage of the controlled release composition is that high local concentrations of the opioid in the gastrointestinal tract are avoided due to the erosion-based release mechanism.

Patients suffering from chronic pains very often require a high daily dosage of an analgesic. If such a high dosage of an opioid should be given only once or twice daily, the release from the composition must be safe. The composition should also be storage stable with respect to chemical and physical stability.

Morphine is probably one of the most commonly used analgesics in the control of severe pain. Due to the short half-life of morphine of approximately 2 hours, the analgesic must be administered frequently, e.g. every 3-4 hours to maintain a patient pain free. This regime may require a 2 a.m. dose to prevent early morning recurrence of pain.

To obtain therapeutic plasma concentrations with less frequent dosing, effective controlled release analgesics are under continuous development. An ideal controlled release analgesic should exhibit the following properties: prevent pain "break-through", eliminate major plasma concentration fluctuations, produce prolongation of effective drug levels, produce effective analgesia without unwanted side effects such as sedation.

In other words, in addition to a less frequent administration, the real challenge in controlled release delivery may be expressed by the goal of decreasing the incidence of adverse effects and at the same time increasing the effect of the treatment. This can only be obtained by an interaction between the specific pharmacological properties of the active ingredient and the composition.

Many controlled release products on the market suffers from the lack of a true controlled release. In fact, Dolcontin®, which covers most of the market for sustained morphine, results in a plasma profile rather similar with an immediate release dosage formulation only with a slight decrease in the initial burst. During the repeated administration, the plasma concentration with this product will necessarily exhibit the undesired peaks and troughs. This may be avoided with the opioid composition according to the present invention.

Controlled release is not only the effect of prolonging the release of active ingredient from the composition by increasing the dosage and decreasing the initial burst. The optimised effect is only obtained when the right balance is obtained between the maximum concentration, the duration of the time where the plasma concentration is above the minimum therapeutic level and the administered dosage.

High concentrations or a fast rise in the concentration of morphine is one important factor resulting in side effects including the risk of getting addicted to morphine. The fear of addiction is often a major obstacle for initiation of the otherwise effective pain treatment with morphine both in the view of the clinical personnel as well as in the view of the patients themselves.

High concentrations during longer periods induce resistance on receptor level and should also be avoided. By "high" is here meant any plasma concentration above the pain relieving level. Other important side effects of morphine are the respiratory depressing effect and sedation; both are highly correlated to the plasma concentration. In addition, memory and motor control, important aspects in relation with long term treatment, may already be present within the therapeutic level and accordingly, any unnecessary high concentration of morphine should be avoided.

According to the present invention it is possible to obtain a composition, which is effective in treating pain and at the same time have one or more of the following advantages: a relative low maximal serum concentration of the opioid and pain relieving effect, relative decreased average serum concentrations and pain relieving effect, minimal concentrations of opioid and pain relieving effect. Each of these factors may be associated with a minor risk of side effects. This conclusion is be supported by a less frequently reported side effects by the patients receiving such a composition in a clinical study comparing controlled release compositions having a non-zero order dissolution profile. Adverse events to be reported in such study include sedation, nausea, dizziness, vertigo, obstipation, urine retention, itching, perspiration, dry mouth. It is generally acknowledged that the most of the broad variety of adverse effects of morphine correlate with the dosage.

Accordingly, a limitation of the maximal concentration as well as the duration of a sufficient concentration is of great benefit for every patient. On the other hand, in chronic pain treatment with morphine, too low concentrations will immediately result in the need for additional rescue medication leading to an increase in the overall dosage, and in the end, to a higher incident of dose dependent side effects. Also in this respect, a formulation according to the present invention is expected to result in the decrease in maximal concentration without a decrease in pain relieving effect. If the controlled release composition is not optimal, the final treatment regimen for the patient including the rescue medication may resemble an ordinary treatment and only few benefits are obtained.

With respect to safety and side effects, many controlled release formulations are only compared with immediate release formulations. The formulation according to the present invention addresses all the problems of a sustained release formulation by releasing a steady and accurately predictable flow of the opioid.

The term "opioid" as used herein denotes a group of active substances that are, to a varying degree, opium- or morphine-like in their properties. The term includes natural and synthetic opioids as well as active metabolites such as, e.g. morphine 6-glucuronide, morphine 3-glucuronide, and mixtures thereof. Pharmaceutically acceptable salts, complexes, solvates and anhydrates thereof, and mixtures thereof are also within the definition of opioids.

In those cases, where the active substance is dispersed in the matrix, it is present in any of its crystalline, polymorphous or amorphous forms or mixtures thereof.

In specific embodiments, the active substance may at least partially be present in solid form in the dispersion, i.e. some of the active substance may be dissolved in the polymer (such as, e.g., polyethylene oxide) provided that at least a part is still present on solid form.

In the pharmaceutical technology (and in the present context), the term "solid dispersion" also embraces semi-solid dispersions. By the term is understood the finely dispersed distribution of one or more solids, e.g. an active substance like morphine, in an inert solid or semi-solid carrier. The active substance may be present in molecular dispersed form, i.e. as a solid solution, in fine crystalline dispersed form, in a glassy amorphous phase or dispersed as a fine amorphous powder. Eutectic mixtures, i.e. crystalline structures of active substances and carriers are also encompassed in the definition of "solid dispersions". Normally, the mean particle size is used to classify dispersed system. A colloidal dispersion is when the dispersed phase has a particle size between about 1 and about 1000 nm and a coarsely dispersion has a mean particle size of at least about 1000 nm and a molecular dispersion has a particle size below about 1 nm. Combinations between the various states are very likely and the most dominating character can be determined by X-ray diffraction spectra or differential thermoanalysis.

In specific aspects of the present invention some of the active substance may be present in a molecular dispersion such as, e.g., in the form of a solid or semi-solid solution.

In a preferred aspect of the invention, a composition comprises morphine that at least partially is present in amorphous form with a mean particle size of at least about 0.01 µm such as, e.g., from about 0.01 µm to about 500 µm, from about 0.05 µm to about 500 µm, from about 0.1 µm to about 500 µm, from about 0.5 µm to about 500 µm, about 1 µm to about 500 µm, typically from about 0.5 µm to about 300 µm, more typically from about 1 µm to about 200 µm, especially from about 1 µm to about 100 µm.

In general, the opioids are readily absorbed from the gastrointestinal tract after oral administration. Many opioids like e.g. morphine are subject to a first-pass metabolism in the liver. The half-life of morphine is about 1.5 to 2 hours, but morphine is metabolised to active metabolites, which have a longer half-life. The average duration of action of a single dose of 10 mg of e.g. oral morphine is about 4-5 hours (given as a plain tablet composition).

The dosage of the opioid(s) contained in a controlled release composition according to the invention depends on the particular opioid in question. With respect to morphine an amount corresponding to from about 5 to about 800 mg of morphine sulfate is suitable. Alternatively, the dosage form (i.e. the composition) may contain a molar equivalent amount of another morphine salt (i.e. the hydrochloride etc.).

Examples of opioids suitable for use in a composition according to the present invention are:

Alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene, sufentanil, tilidine, tramadol, and pharmaceutically acceptable salts, complexes, solvates or anhydrates thereof, and mixtures thereof.

The term "pharmaceutically acceptable salts" of an opiod includes alkali metal salts such as, e.g., sodium or potassium salts, alkaline earth metal salts such as, e.g., calcium and magnesium salts, and salts with organic or inorganic acid like e.g. hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc.

The term "solvates" includes hydrates or solvates wherein other solvates than water are involved such as, e.g., organic solvents like chloroform and the like.

Furthermore, the opiod such as morphine may be in any of its crystalline, polymorphous or amorphous forms.

The present inventors have applied a novel method for controlling the release of an active substance from a pharmaceutical composition. The method involves controlling the release of at least one therapeutically, prophylactically and/or diagnostically active substance into an aqueous medium by erosion of at least one surface of a pharmaceutical composition comprising i) a matrix composition comprising a) polymer or a mixture of polymers, b) an active substance and, optionally, c) one or more pharmaceutically acceptable excipients, and ii) a coating having at least one opening exposing at the one surface of said matrix, the coating comprising a) a first cellulose derivative which has thermoplastic properties and which is substantially insoluble in the aqueous medium in which the composition is to be used, and at least one of b) a second cellulose derivative which is soluble or dispersible in water, c) a plasticizer, and d) a filler, the method comprising adjusting the concentration and/or the nature of the ingredients making up the matrix composition in such a manner that the diffusion rate of the aqueous medium into the matrix composition corresponds to about 100%±30% such as, e.g. about 100%±25%, about 100%±20%, about 100%±15% or about 100%±10% or about 100% of the dissolution rate of the matrix composition so as to obtain a zero order release of at least about 60% w/w such as, e.g. at least about 65% w/w at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

Details concerning the method and the pharmaceutical compositions are described herein.

In a specific embodiment of the invention the polymer mentioned under a) is a substantially water soluble or crystalline polymer or a mixture of substantially water soluble and/or crystalline polymers.

Controlled Release

During the last decades many different systems for modifying the release of an active drug substance from a pharmaceutical composition have been developed. Most of them aim at obtaining a zero or a first order release rate of the active substance from the composition. Zero order release rate (i.e. constant release of the active substance with time) seems to be very difficult to obtain from a pharmaceutical composition. The present invention is based on a polymeric matrix composition, which is construed to deliver the active substance in a zero order release manner. The present invention is a further development based on the Applicant's previously described drug delivery systems, see e.g. EP-B-0 406 315, EP-B-0 493 513, EP-B-0 740 310 and WO 99/51208 the disclosure of which is hereby incorporated by reference.

In particular, it has surprisingly been found that it is possible to obtain zero order release from a polymeric matrix composition without any content of a water dispersible or water soluble surface active agent or a mixture of such surface active agents which has at least one domain which is compatible with the polymer in the polymer matrix composition and at least one other domain which is substantially lipophilic and which has a melting point that is lower than the polymer used in the polymeric matrix composition. The presence of such a substance (e.g. like PEG 400 monostearate or PEG 2000 monostearate) has been contemplated to function as a so-called repair medium. Such a repair medium has a substantially hydrophilic domain, which gives it affinity to the (crystalline) polymeric phase, thereby filling in domains between grains and cracks in the polymer matrix and reducing the water affinity of these domains and in the polymer matrix itself. Water diffusion in the interface between the polymer crystals is thereby substantially eliminated, thus substantially limiting diffusion of water into the composition to the surface layer of the matrix, so that erosion of the composition is predominantly effected by the dissolving action of the aqueous phase on a surface or surfaces of the composition exposed to the aqueous medium. In other words a repair medium seems to prevent the diffusion of water in the polymer matrix composition.

However, in certain cases, the present inventors have observed that inclusion of a water soluble surface active agent has a negative impact on the mobility and/or stability of a composition.

The present inventors have found that it is possible to obtain a zero order release from a polymer matrix composition although water may be able to diffuse into the matrix. When water diffuse into the polymer matrix composition a resulting boundary layer (or swelling layer) can be formed at the surface of the matrix composition, which is exposed to the aqueous medium. In general the diffusion of an active substance through such a boundary layer is important for the release of an active substance and, accordingly, the thickness of the boundary layer is important for the release rate. However, the present inventors have found that it is possible to eliminate or substantially eliminate the impact of the boundary layer on the release rate of the active substance from a polymer matrix composition by ensuring that the thickness of the boundary layer is relatively small and/or that the release of the active substance from a polymer matrix composition is governed by erosion of the composition and the diffusion of the active substance through the boundary layer, if any, has no or only a small impact on the overall release rate.

The present inventors have found that when water is allowed to diffuse into a polymer matrix composition zero order release is obtained when the release rate is governed or controlled by erosion of a constant surface area per time unit. In order to ensure that the erosion of the polymer matrix composition is the predominant release mechanism, the inventors have found that it is necessary to provide a polymer matrix composition which has properties that ensures that the diffusion rate of water into the polymer matrix composition substantially corresponds to the dissolution rate of the polymer matrix composition into the aqueous medium. Thus, by adjusting the nature and amount of constituents contained in the polymer matrix composition along this line the present inventors have obtained polymer matrix compositions, which release the active substance by a zero order release mechanism. The compositions employed are coated in such a manner that at least one surface is exposed to the aqueous medium and this surface has a substantially constant or controlled surface area during erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

Accordingly, the present invention provides a method for controlling the release of at least one therapeutically, prophylactically and/or diagnostically active substance into an aqueous medium by erosion of at least one surface of a pharmaceutical composition comprising i) a matrix composition comprising a) polymer or a mixture of polymers, b) an active substance and, optionally, c) one or more pharmaceutically acceptable excipients, and ii) a coating having at least one opening exposing at the one surface of said matrix, the coating comprising a) a first cellulose derivative which has thermoplastic properties and which is substantially insoluble in the aqueous medium in which the composition is to be used, and at least one of b) a second cellulose derivative which is soluble or dispersible in water, c) a plasticizer, and d) a filler, the method comprising adjusting the concentration and/or the nature of the ingredients making up the matrix composition in such a manner that the diffusion rate of the aqueous medium into the matrix composition corresponds to about 100%±30% such as, e.g. about 100%±25%, about 100%±20%, about 100%±15% or about 100%±10% or about 100% of the dissolution rate of the matrix composition so as to obtain a zero order release of at least about 60% w/w such as, e.g. at least about 65% w/w at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

As mentioned above, in a specific embodiment of the invention, the polymer a) is a substantially water soluble or crystalline polymer or a mixture of substantially water soluble and/or crystalline polymers.

By use of such a method it is possible already during the developmental work to test various polymer matrix compositions with respect to diffusion rate of water into the composition and to dissolution rate of the polymer matrix composition in an aqueous medium. Based on such results adjustment of e.g. the concentration and/or nature of the individual constituents in the composition may be performed until the diffusion rate balance the dissolution rate. In such a manner, a relatively simple instrument has been provided in order to ensure a zero order release rate from the final composition.

In another aspect, the invention relates to a pharmaceutical composition for controlled release of at least one therapeutically, prophylactically and/or diagnostically active substance into an aqueous medium by erosion of at least one surface of the composition, the composition comprising
i) a matrix composition comprising a) a polymer or polymers, b) an active substance and, optionally, c) one or more pharmaceutically acceptable excipients, and
ii) a coating having at least one opening exposing at the one surface of said matrix, the coating comprising
   a) a first cellulose derivative which has thermoplastic properties and which is substantially insoluble in the aqueous medium in which the composition is to be used,
and at least one of
   b) a second cellulose derivative which is soluble or dispersible in water,
   c) a plasticizer, and
   d) a filler,
and the concentration and/or the nature of the ingredients making up the matrix composition has been adjusted in such a manner that the diffusion rate of the aqueous medium into the matrix composition corresponds to about 100%±30% such as, e.g. about 100%±25%, about 100%±20%, about 100%±15% or about 100%±10% or 100% of the dissolution rate of the matrix composition so as to obtain a zero order release of at least about 60% w/w such as, e.g. at least about 65% w/w at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

As mentioned before, in a specific embodiment, the polymer a) is a substantially water soluble or crystalline polymer or a mixture of substantially water soluble and/or crystalline polymers.

Matrix Composition

The pharmaceutical composition according to the invention comprises a matrix composition comprising a) a polymer or a mixture of polymers,
   b) an active substance and, optionally,
   c) one or more pharmaceutically acceptable excipients.

In a specific embodiment, the polymer is a substantially water soluble or crystalline polymer or a mixture of substantially water soluble and/or crystalline polymers.

Polymers

Suitable polymers for use according to the invention typically comprises a polyglycol, e.g. in the form of a homopolymer and/or a copolymer. In a specific embodiment the polymer is substantially water soluble or crystalline polymer or a mixture of substantially water soluble and/or crystalline polymers. Suitable polymers for use in a composition according to the invention are polyethylene oxides and/or block copolymers of ethylene oxide and propylene oxide. Polyethylene oxides which are suitable for use in the matrix composition are those having a molecular weight of from about 20,000 daltons, such as, e.g., from about 20,000 to about 700,000 daltons, from about 20,000 to about 600,000 daltons, from about 35,000 to about 500,000 daltons, from about 35,000 to about 400,000 daltons, from about 35,000 to about 300,000 daltons, from about 50,000 to about 300,000 daltons, such as, e.g. about 35,000 daltons, about 50,000 daltons, about 75,000 daltons, about 100,000 daltons, about 150,000 daltons, about 200,000 daltons, about 250,000 daltons, about 300,000 daltons or about 400,000 daltons.

A particular suitable polyethylene oxide is one, which in itself has a suitable balance between the diffusion rate of water into the polymer and a dissolution rate of the polymer. Suitable examples are polyethylene oxides having a molecular weight of about 35,000 daltons, about 50,000 daltons, about 100,000 daltons, about 200,000 daltons, about 300,000 daltons and about 400,000 daltons.

Typical block copolymers of ethylene oxide and propylene oxide may comprise up to about 30% w/w of the propylene oxide based block, and has a molecular weight of about 5,000 daltons, typically about 5,000 to about 30,000 daltons such as, e.g. from about 8,000 to about 15,000 daltons.

Polyethylene glycols (which when the molecular weight is above about 20,000 is denoted polyethylene oxides) are mixtures of condensation polymers of ethylene glycol.

The average molecular weight (MW) can be calculated from the following equation $$MW = (56{,}110 \times 2)/\text{hydroxyl number}$$

Where the hydroxyl number is defined as the number indicating the amount in mg of potassium hydroxide, which is equivalent to the acetic acid, which, by acetylation, is bound by 1 g of a substance.

Mixtures of PEO with different average molecular weights can be used in order to obtain a PEO with a desirable average molecular weight. It is important to note that in such cases it is necessary to use the PEO, which have MW closest to the desired molecular weight. The individual amount of the two PEO necessary to obtain a PEO with a desired MW can be calculated from the hydroxyl number and the equation given above.

The polymer may have a melting point, which is above the body temperature of the human or animal in which the composition is to be used. Thus, the polymer(s) employed in the matrix composition will suitably have a melting point of about 20-120° C. such as, e.g. from about 30 to about 100° C. or from about 40 to about 80° C.

Alternatively to a polymer of a polyglycol type as described above other polymers may be suitable for use in the matrix composition a). Thus, in other embodiments of the invention, the polymer is selected from one or more of the following polymers: water soluble natural polymers such as glucomannan, galactan, glucan, polygalacturonic acid, polyxylane, polygalactomannans, rhanogalacturonan, polyxyloglycan, arabinogalactan, and starch; water soluble polymers such as PVA, PVB, methocel, Eudragit L methyl ester and PHPV; biodegradable polymers such as PHA, and PLA; hydrogels, such as polyacrylic amid, and dextran; copolymers such as polylactic acid with polyglycolic acid; and others such as alginate and pectins including low methylated or methoxylated pectins.

Active Substances

The method for controlling the release of an active system as disclosed herein can also be applied to other active substances than opioids. Thus, a pharmaceutical composition according to the invention may comprise one or more active substances, i.e. substances, which are therapeutically, prophylactically, diagnostically and/or biologically active substance. The term "active substance" as used herein broadly includes any compound, or mixture thereof, that can be delivered from the composition to produce a beneficial result. The active and beneficial agents include pesticides, herbicides, germicides, biocides, algicides, rodenticides, fungicides, insecticides, antioxidants, plant hormone promoters, plant growth inhibitors, preservatives, disinfectants, sterilization agents, catalysts, chemical reactants, fermentation agents, food supplements, nutrients, cosmetics, therapeutically active substances (drugs), vitamins, sex sterilants, fertility inhibitors, fertility promoters, air purifiers, microorganism attenuators, ecological agents and other agents that benefit the environment in which they are used.

In the present context the term "drug substance" includes any physiologically or pharmacologically active substance that produces a localized or systemic effect in animals, in particular in mammals, including humans and primates. Other animals include domestic household, sport or farm animals such as sheep, goats, cattle, horses and pigs, laboratory animals such as mice, rats and guinea pigs, fishes, avians, reptiles and zoo animals. The term "therapeutically, prophylactically and/or diagnostically active substance" includes the term drug substance within its meaning.

In the present context, the term "ecological agent" denotes a non-therapeutic substance that has a biological effect on plants or animals in the environment. An ecological agent may be a pesticide, such as an insecticides or herbicide, a fertilizer a pheromone, a plant growth hormone or the like.

The active substance or substances included in a pharmaceutical composition of the invention may be selected from many therapeutic categories, in particular from substances which may advantageously be administered orally, rectally, vaginally, or administered to a body cavity (e.g. the urinary bladder, kidney pelvis, the gall bladder, the uterus, a central nervous system cavity, infectious/malignant/post-operative cavities, etc.).

Examples of such substances are hypnotics, sedatives, tranquilizers, anti-convulsants, muscle relaxants, analgesics, anti-inflammatory, anaesthetics, anti-spasmodics, anti-ulcer-agents, anti-parasifics, anti-microbials, anti-fungal, cardiovascular agents, diuretics, cytostatics, anti-neoplastic agents, anti-viral agents, anti-glaucoma agents, anti-depressants, sympathomimetics, hypoglycaemics, diagnostic agents, anti-cough, physic energizers, anti-parkinson agents, local anesthetics, muscle contractants, anti-malarials, hormonal agents, contraceptives, anorexic, anti-arthritic, anti-diabetic, anti-hypertensive, anti-pyretic, anti-cholingergic, bronchodilator, central nervous system, inotropic, vasodilator, vasoconstrictor, decongestant, hematine, iron salts and complexes, electrolyte supplement, germicidal, parasympatholytic, para-sympathethomimetic, antiemetic, psychostimulant, vitamin, beta-blockers, H-2 blocker, beta-2 agonist, counterirritants, coagulating modifying agents, stimulants, anti-hormones, drug-antagonists, lipid-regulating agents, uricosurics, cardiac glycosides, ergots and derivatives thereof, expectorants, muscle-relaxants, anti-histamines, purgatives, contrast materials, radio pharmaceuticals, imaging agents, anti-allergic agents.

Examples of specific active substances suitable for use in a composition of the invention are:

Carvedilol, morphine, diclofenac, nifedipine, calcitonin, rivastigmine, methylphenidate, fluoroxetine, rosiglitazone, prednison, prednisolone, codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecainide, alprenolol, proproanolol, nadolol, pindolol, oxprenolol, labetalol, timolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiazide, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, proethazine, cimetidine, ranitidine, sucralfat, papaverine, moxaverine, atropin, butyiscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folid acid heparin, heparin co-factor, diculmarole, warfarin, streptokinase, urokinase, factor VIII, factor IX, vitamin K, thiopeta, busulfan, chlorambucil, cyclophosphamid, melfalan, carmustin, mercatopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogresterone, hydroxiprogesterone, megesterol, noretisteron, tamoxiphen, ciclosporin, sulfosomidine, bensylpenicillin, phenoxymethylpenicillin, dicloxacillin, cloxacillin, flucoxacillin, ampicillin, amoxicillin, pivampicillin, bacampicillin, piperacillin, meziocillin, mecillinam, pivmecillinam, cephalotin, cephalexin, cephradin, cephadroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, tinidazole, trimethoprim, norfloxacin, salazosulfapyridin, aminosalyl, isoniazid, etambutol, nitrofurantoin, nalidixic acid, metanamine, chloroquin, hydroxichloroquin, tinidazol, ketokonazol, acyclovir, interferon idoxuridin, retinal, tiamin, dexpantenol, pyridoxin, folic acid, ascorbic acid, tokoferol, phytominadion, phenfluramin, corticotropin, tetracosactid, tyrotropin, somatotoprin, somatrem, vasopressin, iypressin, desmopressin, oxytocin, chloriongonadotropin, cortison, hydrocortisone, fluodrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityldion, meprobamat, chlordiazepoxid, diazepam, nitrazepam, oxazepam, dikaliumclorazepat, lorazepam, flunitrazepam, alprazolam, midazolam, hydroxizin, chlometiazol, propionmazine, alimemazine, chlorpromazine, levomepromazine, acetophenazine, fluphenazine, perphenazine, prochlorperazine, trifluoperazine, dixyrazine, thiodirazine, periciazin, chlorprothixene, zuclopentizol, flupentizol, thithixen, haloperidol, trimipramin, opipramol, chlomipramin, desipramin, lofepramin, amitriptylin, nortriptylin, protriptylin, maptrotilin, caffeine, cinnarizine, cyclizine, dimenhydinate, meclozine, prometazine, thiethylperazine, metoclopramide, scopolamine, phenobarbital, phenytoine, ethosuximide, primidone, carbamazepine, chionazepam, orphenadrine, atropine, bensatropine, biperiden, metixene, procylidine, levodopa, bromocriptin, amantadine, ambenon, pyridostigmine, synstigmine, disulfiram, morphine, codeine, pentazocine, buprenorphine, pethidine, phenoperidine, phentanyl, methadone, piritramide, dextropropoxyphene, ketobemidone, acetylsalicylic acid, phenazone, phenylbutazone, azapropazone, piroxicam, ergotamine, dihydroergotamine, cyproheptadine, pizitifen, flumedroxon, allopurinol, probenecid, sodiummaurothiomalate auronofin, penicillamine, estradiol, estradiolvalerianate, estriol, ethinylestradiol, dihydrogesteron, lynestrenol, medroxiprogresterone, noretisterone, cyclophenile, clomiphene, levonorgestrel, mestranol, omidazol, tinidazol, ekonazol, chlotrimazol, natamycine, miconazole, sulbentin, methylergotamine, dinoprost, dinoproston, gemeprost, bromocriptine, phenylpropanolamine, sodiumchromoglicate, azetasolamide, dichlophenamide, betacarotene, naloxone, calciumfolinate, in particular clonidine, thephylline, dipyradamol, hydrochlothiazade, scopolamine, indomethacine, furosemide, potassium chloride, morphine, ibuprofen, salbutamol, terbutalin, sulfonylurea, mefformin, insulin, calcitonin, glucagons-like peptide-1, or combinations thereof.

The active substance can be in various forms, such as uncharged molecules, molecular complexes, crystalline forms, amorphous form, polymorphous form, solvates, anhydrates, pharmacologically acceptable salts such as a hydrochloride, hydrobromide, sulfate, laurylate, palmitate, phosphate, nitrite, nitrate, borate, acetate, maleate, tartrate, oleate, and salicylate. For acidic active substance, salts of metals, amines amino acids or organic cations, quaternary ammoniums, can be used. Derivatives of active substances such as esters, ethers and amides which have solubility characteristics suitable for use herein can be used alone or mixed with other drugs. After release of the derivative from the drug delivery system it may be converted by enzymes, hydrolysed by body pH or other metabolic processes to the parent drug or to another biologically active form.

A pharmaceutical composition of the invention may in addition be suitable for the delivery of polypeptides, for example hormones, enzymes such as lipases, proteases, carbohydrates, amylases, lactoferrin, lactoperoxidases, lysozymes, nanoparticles, etc., and antibodies. The composition may also be employed for the delivery of microorganisms, either living, attenuated or dead, for example bacteria, e.g. gastrointestinal bacteria such as streptococci, e.g. S. faecium, Bacillus spp. such as B. subtilis and B. licheniformis, lactobacteria, Aspergillus spp., bifidogenic factors, or viruses such as indigenous vira, enterovira, bacteriophages, e.g. as vaccines, and fungi such as baker's yeast, Saccharomyces cerevisiae and fungi imperfecti. A pharmaceutical composition of the invention may also be used for the delivery of active agents in specialized carriers such as liposomes, cyclodextrines, nanoparticles, micelles and fats.

A further use for which a composition of the invention is suited is the delivery of active substances to animals. Examples of such active substances for veterinary use are antiparasitics, corticosteroids, antibiotics, antiinflammatory agents, growth promoters and permittants, antifungals and antihelmintics.

A pharmaceutical composition of the invention is designed to release the active substance in a controlled manner such as by a zero order release mechanism. Accordingly, the composition is also suitable for a controlled release of an active substance. In the present context the term "controlled release" is used to designate a release a desired rate during a predetermined release period. Terms like "modified", "delayed", "sustained", "prolonged", "extended" etc. release are in the present context synonyms to the term "controlled release".

In an embodiment of the invention, the active substance is a pharmaceutically active powder. The powder typically has a particle size of from about 0.1 µm to about 500 µm, typically from about 0.5 µm to about 300 µm, more typically from about 1 µm to about 200 µm, especially from about 5 µm to about 100 µm.

A pharmaceutical composition according to the invention is—due to the possibility of designing the composition in such a manner that i) a zero order release is obtained and ii) a controlled release during a predetermined time period is obtained—suitable for use for water soluble as well as slightly soluble or insoluble active substances. However, it is contemplated that a composition is especially suitable for use when the at least one therapeutically, prophylactically and/or diagnostically active substance has a solubility of at the most about 3 mg/ml such as, e.g. at the most about 1 mg/ml, at the most about 0.1 mg/ml, at the most about 0.05 mg/ml such as, e.g. at the most about 0.001 mg/ml in water at ambient temperature and/or a prolonged release of the active substance is desired in order to obtain i) a prolonged residence time within the body after administration, ii) a reduced peak plasma concentration in order to avoid peak related side effects, iii) reduced frequency of administration in order e.g. to obtain a better patient compliance, etc.

To this end it seems that substantially hydrophobic active substances tend to result in a decrease in the erosion rate of the matrix composition. Substantially hydrophilic or water-soluble active substances seem to have the opposite effect, i.e. they tend to result in a faster erosion of the matrix.

The at least one therapeutically, prophylactically and/or diagnostically active substance will suitably be present in an amount of up to about 70%, typically up to about 60% or up to about 50%, by weight of the matrix composition. An active substance content of about 60% is contemplated to be the maximum content, which still allows for a sufficient content of the polymer and, when relevant, the pharmaceutically acceptable excipient in the composition. The active substance may, on the other hand, be present in the composition in much smaller amounts, depending on the nature and potency of the active substance in question.

Pharmaceutically Acceptable Excipients
Diffusion and Dissolution Adjusters

As already discussed above, it is important that a composition according to the invention releases at least most of the active substance by a zero order release mechanism. One aspect of research about controlled-release delivery systems involves designing a system, which produces steady-state plasma drug levels. The release of active substance from such systems is also referred to as zero-order drug release kinetics. To meet this objective, numerous design variations have been attempted, and their major controlling mechanisms include diffusion/dissolution.

The release rate of a dissolved or dispersed active substance from a polymeric matrix composition introduced in a specific environment, strongly depends on the nature of the diffusion and sorption processes involving the polymer/environment system and the polymer/active substance system.

The active substance release data may be analysed using Eq. 1 and Eq. 2 where $M_t/M_\infty$ is the fractional drug release, t is the release time, k is a kinetic constant characteristics of the drug/polymer system, $C_d$ is the tracer loading concentration and n is an exponent which characterisers the mechanism of release of the tracers.

$$\frac{M_t}{M_\infty} = k \cdot t^n \quad \text{(Eq. 1)}$$

$$\frac{dM_t}{A \cdot dt} = n \cdot C_d \cdot k \cdot t^{n-1} \quad \text{(Eq. 2)}$$

Clearly, a desirable mechanism for many applications is that which leads to n=1. This characterizes zero-order behaviour. The table below summarizes the general dependence of n on the diffusion mechanism.

| Diffusinal release solute release Exponent (n) | Overall Solute diffusion mechanism | time dependence of rate $(dM_t/d_t)$ |
| --- | --- | --- |
| 0.5 | Fickian diffusion | $t^{-0.5}$ |
| 0.5 < n < 1.0 | Anomalous (non Fickian) diffusion | $t^{n-1}$ |
| 1.0 | Case II Transport | Zero-order (time independent) release |
| n > 1.0 | Super Case II transport | $t^{n-1}$ |

In the case of PEO matrices, the solubility of the polymer can alter the characteristics of the penetrated layer, leading to different behaviours in systems presenting different dissolution features. To control the release of the active agent, there should be a balance between diffusion of the active agent and solubilization of the polymer matrix. The diffusivity of the drug through the matrix, the swelling of the polymer, and its solubilization rate may be biased by changing the molecular weight of the polymer or blending polymer fractions with different molecular weights.

In the following is given examples on suitable excipients that may be added in order to adjust the balance between diffusion and dissolution so as to obtain zero order release rate. The pharmaceutically acceptable excipients suitable for establishing the above-mentioned desired balance, are in the present context also denoted DDAs (Diffusion and Dissolution Adjusters).

Thus, the matrix composition may also comprise one or more pharmaceutically acceptable excipients (DDAs). The function of the at least one pharmaceutically acceptable excipient is to establish the desired balance between on the one hand the diffusion rate of water into the matrix composition and on the other hand the dissolution rate of the matrix composition in an aqueous medium such as, e.g., water. As explained above, a zero order release rate is obtained if that the diffusion rate of the aqueous medium into the matrix composition corresponds to about 100%±30% such as, e.g. about 100%±25%, about 100%±20%, about 100%±15% or about 100%±10% or about 100% of the dissolution rate of the matrix composition. By the term "zero order release" is meant that the release takes place so as to obtain a zero order release of at least about 60% w/w such as, e.g. at least about 65% w/w, at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

In general a test for diffusion of water into the matrix composition and a test for the dissolution of the matrix composition in an aqueous medium are performed using a matrix composition having the desired shape and being prepared analogous to the matrix composition in the final composition. This means that when the final composition is prepared by e.g. injection moulding then the matrix composition to be tested with respect to diffusion and dissolution behaviour is also prepared by injection moulding.

There may be cases where it is not necessary to adjust the matrix composition by adding a pharmaceutically acceptable excipient. Such cases are e.g. when the polymer employed in itself has the desired properties with respect to diffusion of water and dissolution of polymer.

In the experimental section herein examples are given showing that it has been possible to obtain the desired zero order release when a pharmaceutically acceptable excipients has been incorporated into the matrix composition.

Without being bound by any theory it is contemplated that in those cases where a slightly or insoluble active substance is employed then it may be necessary to circumvent the effect from the active substance (with respect to diffusion and/or dissolution of the matrix composition) by adding a very soluble pharmaceutically acceptable excipient. Accordingly, it is contemplated that when the at least one therapeutically, prophylactically and/or diagnostically active substance has a solubility of at the most about 3 mg/ml such as, e.g. at the most about 1 mg/ml, at the most about 0.1 mg/ml, at the most about 0.05 mg/ml such as, e.g. at the most about 0.001 mg/ml in water at ambient temperature then the pharmaceutically acceptable excipient, if present, typically has a solubility of at least 1 mg/ml such as, e.g. at least about 3 mg/ml, at least about 5 mg/ml, at least about 10 mg/ml, at least about 25 mg/ml or at least about 50 mg/ml in water at ambient temperature.

Vice versa, it is contemplated that in those cases where a very soluble active substance is employed then it may be necessary to circumvent the effect from the active substance (with respect to diffusion and/or dissolution of the matrix composition) by adding a slightly or insoluble pharmaceutically acceptable excipient. Accordingly, it is contemplated that when the at least one therapeutically, prophylactically and/or diagnostically active substance has a solubility of at least about 3 mg/ml such as, e.g., at least about 5 mg/ml, at least about 10 mg/ml, at least about 20 mg/ml, at least about 50 mg/ml or at least about 100 mg/ml in water at ambient temperature, then the pharmaceutically acceptable excipients typically has a solubility of at the most about 3 mg/ml such as, e.g., at the most about 1 mg/ml, at the most about 0.1 mg/ml, at the most about 0.05 mg/ml such as, e.g. at the most about 0.001 mg/ml in water at ambient temperature.

There may situations, however, where it also may be suitable to incorporate water-soluble substances (and/or water-insoluble substances) as DDA's irrespective of the solubility of the active substance.

Furthermore, in those cases where the active substance employed has a low solubility in acidic medium, it is contemplated that an inorganic or organic base or substance having an alkaline reaction in aqueous environment is employed as a DDA.

Analogous, in those cases where the active substance employed has a low solubility in alkaline medium, it is contemplated that an inorganic or organic acid or substance having an acidic reaction in aqueous environment is employed as a DDA.

However, other factors than the solubility in water play a role in the erosion process and therefore there may be situations where such factors dominate the solubility factor and then the above-given combinations may be of minor importance.

Suitable pharmaceutically acceptable excipients (DDAs) may be selected from the group consisting of inorganic acids, inorganic bases, inorganic salts, organic acids or bases and pharmaceutically acceptable salts thereof, saccharides, oligosaccharides, polysaccharides, and cellulose and cellulose derivatives.

Alternatively or additionally, a suitable pharmaceutically acceptable excipient is a mono-, di-, oligo, polycarboxylic acid or amino acids such as, e.g. acetic acid, succinic acid, citric acid, tartaric acid, acrylic acid, benzoic acid, malic acid, maleic acid, sorbic acid etc., aspartic acid, glutamic acid etc.

Examples of suitable organic acids include acetic acid/ ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, and pyruvic acid.

Examples of suitable inorganic acids include pyrophosphoric, glycerophosphoric, phosphoric such as ortho and meta phosphoric, boric acid, hydrochloric acid, and sulfuric acid.

Examples of suitable inorganic compounds include aluminium.

Examples of organic bases are p-nitrophenol, succinimide, benzenesulfonamide, 2-hydroxy-2cyclohexenone, imidazole, pyrrole, diethanolamine, ethyleneamine, tris(hydroxymethyl)aminomethane, hydroxylamine and derivates of amines, sodium citrate, aniline, hydrazine.

Examples of inorganic bases include aluminium oxide such as, e.g., aluminium oxide trihydrate, alumina, sodium hydroxide, potassium hydroxide, calcium carbonate, ammonium carbonate, ammonium hydroxide, KOH and the like.

Suitable pharmaceutically acceptable salts of an organic acid is e.g. an alkali metal salt or an alkaline earth metal salt such as, e.g. sodium phosphate, sodium dihydrogenphosphate, disodium hydrogenphosphate etc., potassium phosphate, potassium dihydrogenphosphate, potassium hydrogenphosphate etc., calcium phosphate, dicalcium phosphate etc., sodium sulfate, potassium sulfate, calcium sulfate, sodium carbonate, sodium hydrogencarbonate, potassium carbonate, potassium hydrogencarbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate, calcium tartrate etc.

A suitable inorganic salt for use in a matrix composition of the invention is sodium chloride, potassium chloride, calcium chloride, magnesium chloride etc.

Examples of such excipients are glucose and other monosaccharides, ribose, arabinose, xylose, lyxose, allose, altrose, inosito, glucose, sorbitol, mannose, gulose, idose, galactose, talose, mannitol, fructose, lactose, sucrose, and other disaccharides, dextrin, dextran or other polysaccharides, amylose, xylan, cellulose and cellulose derivatives such as, e.g. microcrystalline cellulose, methyl cellulose, ethyl cellulose, ethylhydroxyethyl cellulose, ethylmethylcellulose, hydroxyethylcellulose, hydroxyethylmethyl cellulose, carboxymethyl cellulose, hydroxypropyl cellulose, hydroxymethylpropyl cellulose, hydroxypropylmethyl cellulose, amylopectin, pectin, starch, sodium starch etc., kaolin, bentonit, acacia, alginic acid, sodium alginate, calcium alginate, gelatin, dextrose, molasses, extract of Irish moss, panwar gum, ghatti gum, mucilage of isapol husk, veegum, glycollate, magnesium stearate, calcium stearate, stearic acid, talc, titanium dioxide, silicium dioxide, clays, croscarmellose, gums, agar etc.

Other Ingredients in the Matrix Composition

The matrix composition may also contain other excipients as well, e.g. in order to improve the technical properties of the matrix composition so that it may be easier to produce or in order to improve the stability of the composition.

A suitable pharmaceutically acceptable excipient for use in a matrix composition of the invention may be selected from the group consisting of fillers, diluents, disintegrants, glidants, pH-adjusting agents, viscosity adjusting agents, solubility increasing or decreasing agents, osmotically active agents and solvents.

Suitable excipients include conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as acacia, sodium alginate, starch, gelatin, saccharides (including glucose, sucrose, dextrose and lactose), molasses, extract of Irish moss, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone such as, e.g., PVP K90 (may be used to improve mixing of the polymer with the other ingredients) or mixtures thereof; lubricants such as talc, magnesium stearate, calcium stearate, staeric acid, hydrogenated vegetable oils, sodium benzoate, sodium chloride, leucine, carbowax 4000, magnesium lauryl sulfate, colloidal silicon dioxide and mixtures thereof, disintegrants such as starches, clays, cellulose derivatives including croscarmellose, gums, aligns, various combinations of hydrogencarbonates with weak acids (e.g. sodium hydrogencarbonate/tartaric acid or citric acid) crospovidone, sodium starch glycolate, agar, cation exchange resins, citrus pulp, veegum HV, natural sponge, bentonite or mixtures thereof; volatile solvents such as alcohols, including aqueous alcohols, petroleum benzine, acetone, ether or mixtures thereof; plasticizers such as sorbitol and glycerine; and others such as cocoa butter, polyethylene glycols or polyethylene oxides, e.g. with a molecular weight of about 1,000-500,000 daltons, typically about 1,000-100,000 daltons, more typically 1,000-50,000 daltons, especially about 1,000-10,000 daltons, in particular about 1,500-5,000 daltons, and mixtures thereof, hydrogenated vegetable oils, glycerinated gelatin or mixtures thereof.

The matrix composition may in addition include a cellulose derivative, e.g. a cellulose derivative selected from the group consisting of methylcellulose, carboxymethylcellulose and salts thereof, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose. Of these cellulose derivatives, hydroxypropylmethylcellulose and methylcellulose are preferred for incorporation in the matrix composition.

Furthermore, the matrix composition may comprise one or more agents selected from the group consisting of sweetening agents, flavouring agents and colouring agents, in order to provide an elegant and palatable preparation. Examples of colouring agents are water soluble FD&C dyes and mixtures thereof with corresponding lakes and direct compression sugars such as Di-Pac from Amstar. In addition, coloured dye migration inhibitors such as tragacanth, acacia or attapulgite talc may be added. Specific examples include Calcium carbonate, Chromium-cobalt-aluminium oxide, ferric ferrocyanide, Ferric oxide, Iron ammonium citrate, Iron (III) oxide hydrated, Iron oxides, Magnesium carbonate, Titanium dioxide.

Examples of suitable fillers are also dextrin, sucralfate, calcium hydroxyl-apatite, calcium phosphates and fatty acid salts such as magnesium stearate.

The filler may be added in an amount so that the combination of the filler and the active substance comprises up to about 60%, typically up to about 50%, by weight of the first composition.

In order to soften the carrier system, a plasticiser may be incorporated in the composition. A suitable plasticizer is selected from the group consisting of phosphate esters; phthalate esters; amides; mineral oils; fatty acids and esters; fatty alcohols, vegetable oils and hydrogenated vegetable oils including acetylated hydrogenated cottonseed glyceride and acetylated hydrogenated soybean oil glycerides; acetyl tributyl citrate, acetyl triethyl citrate, Castor oil, diacetylated monoglycerides, dipropylene glycol salicylate glycerin, glyceryl cocoate, mono- and di-acetylated monoglycerides, nitrobenzene, carbon disulfide, β-naphtyl salicylate, phthalyl glycolate, diocyl phthalate; sorbitol, sorbitol glyceryl tricitrate; sucrose octaacetate; a-tocopheryl polyethylene glycol succinate, phosphate esters; phthalate esters; amides; mineral oils; fatty acids and esters; fatty alcohols; and vegetable oils, fatty alcohols including cetostearyl alcohol, cetyl alcohol, stearyl alcohol, oleyl alcohol and myristyl alcohol; methyl abietate, acetyl tributyl citrate, acetyl triethyl citrate, diisooctyl adipate, amyl oleate, butyl ricinoleate, benzyl benzoate, butyl and glycol esters of fatty acids, butyl diglycol carbonate. butyl oleate, butyl stearate. di(beta-methoxyethyl) adipate, dibutyl sebacate, dibutyl tartrate, diisobutyl adipate, dihexyl adipate, triethylene glycol di(beta-ethyl butyrate), polyethylene glycol di(2-ethyl hexoate), diethylene glycol monolaurate, monomeric polyethylene ester, hydrogenated methyl ester of rosin, methoxyethyl oleate, butoxyethyl stearate, butyl phthalyl butyl glycolate, glycerol tributyrate, triethylene glycol dipelargonate, beta-(p-tert-amyl phenoxy)ethanol, beta(p-tert-butylphenoxy)ethanol, beta-(p-tert-butylphenoxyethyl)acetate, bis(beta-p-tert-butylphenoxydiethyl)ether, camphor, Cumar W-1, Cumar MH-1, Cumar V-1, diamyl phthalate, (diamylphenoxy) ethanol, diphenyl oxide, technical hydroabietyl alcohol, beckolin, benzene hexahydrochlonde, Clorafin 40, Piccolastic A-5, Piccalastic A-25, Flexol B400, Glycerol alfa-methyl alfa-phenyl ether, chlorinated naphthalene, HB-40, monoamylphthalate. Nevillac 10 o-nitrodiphenyl and Paracril 26.

Preferred anti-oxidative agents include TPGS due to surfactant properties, BHA, BHT, t-butyl hydroquinone, calcium ascorbate, gallic acid, hydroquinone, maltol, octyl gallate, sodium bisulfite, sodium metabisulfite, tocopherol and derivates thereof, citric acid, tartaric acid, and ascorbic acid. Other antioxidants include trivalent phosphorous like e.g phosphite, phenolic antioxidants, hydroxylamines, lactones such as substituted benzofuranones. Hindered phenols, thio-synergists and/or hindered amines are useful for the long-term stability for polymers, whereas the following antioxidants are suitable for use also in situation where the active substance is subject to oxidation: adds (ascorbic acid, erythorbic acid, etidronic acid, gallic acid, hypophosphorous acid, nordihydroguairetic acid, propionic acid etc.), phenols (e.g. BHA, BHT, t-butyl hydroquinone, dodecyl gallate, octyl gallate, 1,3,5-trihydroxybenzene), organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopheryl acetate, d-α-tocopheryl acetate, dl-α-tocopheryl acetate. However, other anti-oxidative agents known in the art may be used according to the present invention.

pH Dependant Release

In some situations it may be convenient that the composition releases the active substance in a pH dependant manner. As described in e.g. WO 99/51208 a pH dependant release can be obtained by inclusion of a so-called release rate modifier. The release rate modifier is preferably selected from materials conventionally used in the pharmaceutical industry to produce enteric coatings. A number of different types of compounds suitable for use as enteric coatings are known in the art; see e.g. *Remington's Pharmaceutical Sciences*, 18$^{th}$ Edition, 1990. Release modifiers may in particular be selected from one of three general classes, namely cellulose derivatives, methacrylic add polymers and modified gelatine compounds. Preferred release modifiers include cellulose acetate phthalate, polyvinyl acetate phthalate, hydroxypropyl methylcellulose phthalate and hydroxypropyl methylcellulose acetate succinate, as well as methacrylic acid copolymers. Modified gelatine compounds include gelatine treated with e.g. formaldehyde or glutaraldehyde.

Examples of commercially available polymers suitable as release modifiers are EUDRAGIT® L and EUDRAGIT® S, available from Röhm GmbH, Germany, and enteric coating agents available from Shin-Etsu Chemical Co., Japan. The release modifier will typically be present in the composition in an amount of about 0.1-10%, based on the weight of the matrix, preferably about 0.54%, e.g. about 1-3%, such as about 1.5-2.0%. If desired, a suitable mixture of more than one release modifier may be used in order to obtain a desired release profile in any given composition.

The release modifier enables a difference in release of the active substance/erosion of the matrix dependant on pH.

Shape

The geometric form of the composition is important for the obtainment of the above-mentioned controlled zero order. Thus, in a preferred version of the invention, the pharmaceutical composition of the invention has a geometric shape, which enables a substantially constant surface area to become exposed during erosion of the matrix.

In order to achieve a higher plasma concentration 5-10 hours after administration it is contemplated that a shape is suitable that exposes an increasing surface area during the first 1-3 hours and then exposes a constant surface area. Examples of such shapes are given in FIG. 1B.

Specific examples of compositions with different shapes and sizes are:

| Batch | Length [mm] | Diameter [mm] | Vol [mm³] |
|---|---|---|---|
| 01-0034-042 | 7.5 | 5.05 | 150 |
| 01-0035-042 | 6.0 | 5.64 | 150 |
| 01-0043-042 | 9.0 | 4.6 | 150 |

The following table describes formulations having a cylindrical form and oval openings in both ends

| Batch | Length [mm] | Vol [mm³] | Longest/shortest diameter [mm] | |
|---|---|---|---|---|
| 01-0075-042 | 6.0 | 150 | 8.74 | 3.64 |
| 01-0076-042 | 7.5 | 150 | 7.82 | 3.21 |

The coated compositions obtained were open at two opposite ends.

The area for an open end is calculates as the volume/length of the cylindrical formulations.

Coating

The pharmaceutical composition may thus have the shape of a cylindrical rod, which is provided with a coating, which is substantially insoluble in and impermeable to fluids such as body fluids during the intended release period, the coating having an opening at one or both ends. Polymers useful as coatings are preferably those, which are possible to process by extrusion, solution or in the form of a dispersion. Most preferred are those, which are available in a food grade or a pharmaceutical grade quality. Examples of such polymers are cellulose acetate, polyamide, polyethylene, polyethylene terephthalate, polypropylene polyurethane, polyvinyl acetate, polyvinyl chloride, silicone rubber, latex, polyhydroxybutyrate, polyhydroxyvalerate, teflon, polylactic acid or polyglycolic acid and copolymers thereof, copolymers such as ethylene vinyl acetate (EVA), styrene-butadienestyrene (SBS) and styrene-isoprene-styrene (SIS).

The coating may also be a coating, which is substantially soluble in and permeable to fluids such as body fluids during the intended release period provided that the coating dissolves so much slower than the matrix composition that the coating remains intact until the matrix has eroded and released the active substance. Examples of suitable polymers include polyols as described herein.

The coating may further comprise any of the above-mentioned matrix materials in a form, which erodes at a substantially slower rate than the rest of the matrix. The coating may thus comprise a matrix of one or more substantially water-soluble crystalline polymers and, optionally, a non-ionic emulsifier, the coating being one which is eroded in the aqueous phase at a substantially slower rate than the matrix composition comprising the active substance, whereby a substantially constant area of the matrix composition comprising the active substance is exposed during erosion of the matrix composition, and whereby the coating is substantially eroded upon erosion of the matrix composition comprising the active substance. Such a coating will be designed so that its longitudinal erosion rate is substantially the same as the longitudinal erosion rate of the matrix, whereby the matrix and the coating will erode longitudinally towards the centre of the composition at substantially the same rate. Thus, when the matrix composition has been completely eroded by the aqueous medium, the coating will also be substantially completely eroded. A matrix composition having such a coating has the obvious advantage of being completely biodegraded upon release of the active substance. Such a coating will typically be a combination of a polyethylene glycol and a mixture of, for example, polyethylene glycol 400 monostearate or another non-ionic emulsifier, and may also include a filler. The content of the mixture of non-ionic emulsifiers and the filler in the coating will be determined in each particular case according to the characteristics, e.g. erosion rate and size, of the matrix comprising the active substance.

In an embodiment of the invention, the coating is one, which disintegrates or crumbles after erosion of the matrix. A coating of this type will remain intact as long as it is supported by the matrix containing the active substance, but it lacks the ability to remain intact after erosion of the matrix, because it then disintegrates or crumbles, so that it will not remain in e.g. a human or animal for any significant amount of time after the complete erosion of the matrix and the release of the active substance.

The coating may also be an enteric coating employing methacrylates, a co-polymer of methacrylate-galactomannan etc.

In an interesting embodiment, the controlled release composition of the invention further comprises a coating having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled. Coatings of this type are described in WO 95/22962, to which reference is made and which is incorporated herein by reference. These coatings comprise:

(a) a first cellulose derivative which has thermoplastic properties and which is substantially insoluble in the aqueous medium in which the composition is to be used, e.g. an ethylcellulose such as ethylcellulose having an ethoxyl content in the range of 44.5-52.5%, or cellulose acetate, cellulose propionate or cellulose nitrate;

and at least one of:

(b) a second cellulose derivative which is soluble or dispersible in water, e.g. a cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose;

(c) a plasticizer, e.g. selected from the group consisting of phosphate esters; phthalate esters; amides; mineral oils; fatty acids and esters thereof with polyethylene glycol, glycerin or sugars; fatty alcohols and ethers thereof with polyethylene glycol, glycerin or sugars; and vegetable oils; or a non-ionic surfactant; and (d) a filler, e.g. selected from conventional tablet or capsule excipients such as diluents, binders, lubricants and disintegrants.

The use of a plasticizer will often be desirable in order to improve the processibility of the ethylcellulose or the first cellulose derivative. The plasticizer may also be a non-ionic surfactant, e.g. a non-ionic surfactant selected from the group consisting of diacetylated monoglycerides, diethylene glycol monostearate, ethylene glycol monostearate, glyceryl monoleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monoleate, sorbitan monopalmitate, sorbitan monostearate, sorbitan sesquioleate, sorbitan trioleate, sorbitan tristearate and sucrose esters; nitrobenzene, carbon disulfide, β-naphtyl salicylate, phthalyl glycolate, dioctyl phthalate.

Other suitable plasticizers appear from EP-B-0 746 310 to which reference is made.

Pharmaceutical Composition

As mentioned above a pharmaceutical composition according to the invention is a coated matrix composition from which the active substance is released by a zero order release mechanism.

A composition according to the invention containing a drug substance is typically for oral administration and may be in the form of a tablet or a capsule or in the form of a multiple unit dosage form. Due to the possibility of controlling the release rate of the active substance the composition may be adapted for oral administration 1-6 times a day, normally 1-4 times daily such as 1-3 times, 1-2 times or 1 times daily. The technology may also provide compositions for administration only once or twice daily. In the present context the term "once daily" is intended to mean that it is only necessary to administer the pharmaceutical composition once a day in order to obtain a suitable therapeutic and/or prophylactic response; however, any administration may comprise co-administration of more than one dosage unit, such as, e.g. 2-4 dosage units if the amount of active substance required may not be formulated in only one composition or if a composition of a smaller size is preferred.

The dosage of the active substance depends on the particular substance, the age, weight condition etc. of the human or animal that will be treated with the composition etc. All such factors are well known to a person skilled in the art.

The controlled release of the active substance is caused by erosion at a substantially constant rate of a surface or surfaces of the composition The rate at which the active substance is released from the matrix is a predetermined rate, i.e. a rate, which is controllable over a certain period of time. The release rate required in each particular instance may inter alia depend on the amount of active substance to be released for it to exert the desired effect, as well as on the overall dosage of the active substance contained in the matrix. The substance of which the matrix is composed and the distribution of the active substance in the matrix may therefore be selected according to one or more of these criteria to ensure the desired level of release of the active substance.

Due to the controlled release of the active substance obtainable from the pharmaceutical composition of the invention, it is possible to obtain a substantially constant rate of release of the active substance over a specific period of time, corresponding to the dosage necessary for the treatment in question, so that adherence to a strict dosage regimen, e.g. requiring administration of a drug at set intervals up to several times a day, may be dispensed with.

Furthermore, it is possible to include two or more different active substances in the pharmaceutical composition of the invention, and the two or more different active substances may be adapted to be released at different concentrations and/or intervals, thus making it easier for patients to follow a prescribed regimen.

An additional advantage of a pharmaceutical composition of the invention, compared to other known controlled release compositions, is that it may be produced by relatively simple and inexpensive methods.

Furthermore, a pharmaceutical composition according to the invention allows for the incorporation of high concentrations of the active substance relative to the size of the delivery system. This is obviously a great advantage, notably when the composition is to be used for the delivery of a therapeutically, prophylactically and/or diagnostically active substance, since it allows for the delivery of the required amount of the active substance without the size of the composition being unnecessarily large. In addition, sparingly soluble or non-soluble active substances may be readily incorporated into a composition of the invention. A composition of the invention may thus be used for the delivery of, for example, sparingly soluble or non-soluble pharmaceutical powders which can otherwise be difficult to administer.

As mentioned above, the release of the active substance from the pharmaceutical composition corresponds to a substantially zero order release determined by in vitro dissolution test according to USP. The substantially zero order release is obtained in a time period of at least 1 hours such as, e.g. at least 2 hours, at least 3 hours, at least 4 hours or at least 5 hours, or in a time period of at least 5 hours such as, e.g. at least 6 hours, at least 7 hours, at least 8 hours, at least 9 hours or at least 10 hours.

Opiod Compositions

In the experimental section herein examples are given on suitable morphine containing compositions, which are based on the concept described herein.

In an embodiment the invention relates to a pharmaceutical composition for controlled release of an opioid or a pharmaceutically acceptable salt or metabolite thereof into an aqueous medium by erosion of at least one surface of the composition, the composition comprising i) a matrix composition comprising a) polymer or a mixture of polymers, b) an opioid and, optionally, c) one or more pharmaceutically acceptable excipients, and ii) a coating having at least one opening exposing at the one surface of said matrix, the coating comprising a) a first cellulose derivative which has thermoplastic properties and which is substantially insoluble in the aqueous medium in which the composition is to be used, and at least one of b) a second cellulose derivative which is soluble or dispersible in water, c) a plasticizer, and d) a filler, and the concentration and/or the nature of the ingredients making up the matrix composition has been adjusted in such a manner that the diffusion rate of the aqueous medium into the matrix composition corresponds to about 100%±30% such as, e.g. about 100%±25%, about 100%±20%, about 100%±15% or about 100%±10% or about 100% of the dissolution rate of the matrix composition so as to obtain a zero order release of at least about 60% w/w such as, e.g. at least about 65% w/w at least about 70% w/w, at least about 75% w/w, at least about 80% w/w, at least about 85% w/w, at least about 90% w/w, at least about 95% w/w or at least about 97 or 98% w/w of the active substance from the pharmaceutical composition when subject to an in vitro dissolution test as described herein.

Especially suitable polymers are those of the polyol type described herein such as, e.g. polyethylene glycol, a polyethylene oxide and/or a block copolymer of ethylene oxide and propylene oxide. The polymers have a molecular weight of from about 20,000 daltons, such as, e.g., from about 20,000 to about 700,000 daltons, from about 20,000 to about 600,000 daltons, from about 35,000 to about 500,000 daltons, from about 35,000 to about 400,000 daltons, from about 35,000 to about 300,000 daltons, from about 50,000 to about 300,000 daltons, such as, e.g. about 35,000 daltons, about 50,000 daltons, about 75,000 daltons, about 100,000 daltons, about 150,000 daltons, about 200,000 daltons, about 250,000 daltons, about 300,000 daltons or about 400,000 daltons.

From the examples it is seem that employment of PEO 200,000 leads to a suitable composition.

Suitable pharmaceutically acceptable excipients are also described herein such as, e.g. inorganic acids, inorganic bases, inorganic salts, organic acids or bases and pharmaceutically acceptable salts thereof, saccharides, oligosaccharides, polysaccharides, and cellulose and cellulose derivatives. The organic acid may be a mono-, di-, oligo or polycarboxylic acid such as, e.g. acetic acid, succinic acid, citric acid, tartaric acid, acrylic add, benzoic acid, malic acid, maleic acid etc.

From the examples it is seem that employment of mannitol or a base like aluminium oxide leads to a suitable composition.

Accordingly, in a specific embodiment the invention relates to a pharmaceutical composition in which the matrix composition comprises morphine, PEO 200,000 and mannitol and/or aluminium oxide.

Multiple Units Composition

The pharmaceutical composition according to the invention may furthermore be used in the preparation of a multiple units pharmaceutical composition, e.g. in the form of a capsule or tablet. A multiple units pharmaceutical composition is a composition, which comprises a multiplicity of individual units in such a form that the individual units will be made available upon disintegration of the composition, typically a capsule or tablet, in the stomach of humans or animals ingesting said composition. Thus, in this case, at least some of the individual units in said multiple units pharmaceutical composition will consist of the composition of the invention, the individual units being of a size, which allows them to be incorporated into such a composition.

Preparation

The delivery system as well as the first composition of the invention may be produced by various methods which are either known per se in the pharmaceutical industry or which, for example, are used in the production of polymer-based materials, depending upon the desired embodiment and the materials employed in the composition in question. As mentioned above, one advantage of the composition according to the invention is that it may be produced by methods, which are relatively simple and inexpensive.

A pharmaceutical composition may be produced by, for example, co-extrusion of the coating with the matrix composition and the active substance, extrusion and dip coating, injection moulding and dip coating, or by extrusion or injection moulding and solvent coating by spraying or dipping.

For further details reference is made to the experimental section herein.

Method for Controlling the Release

As mentioned above, the invention also relates to a method for controlling the release of a therapeutically, prophylactically and/or diagnostically active substance from a pharmaceutical composition. To this end all details and particulars described above under the composition aspect applies mutatis mutandi to the method aspect and to other aspects of the invention.

The invention is further illustrated in the following figures and non-limiting examples.

FIG. 2 is the dissolution profile from the composition of Example 1.

METHODS

Figure 1A:
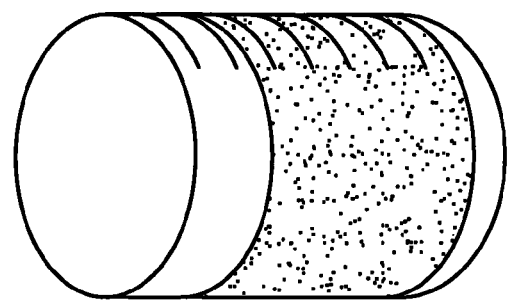
FIG. 1A is a plug holder suitable for use when determining diffusion and dissolution rate. A stopper on the right seals the plug holder, and the swelling layer is formed on the left side on the plug.

Diffusion/Dissolution Studies
Method for Determination of Dissolution Rate of the Matrix A composition according to the invention has properties that ensure that the diffusion rate of water into the polymer matrix substantially corresponds to the dissolution rate of the polymer matrix composition into the aqueous medium. In the following is given a simple method to test these conditions.

The polymers that are suitable for use according to the present invention and which are sufficiently hydrophilic are water-soluble. When contacted with water, a sharp advancing waterfront divides the intact and not penetrated matrix from a swollen front. Under stationary conditions, a constant thickness surface layer is formed by the swollen polymer and by a high concentration of polymer in solution.

In fact, once the hydrodynamic external conditions are defined, a stationary state is reached where the rate of penetration of the moving boundary equals the rate of removal of the polymer at the external surface.

The time lapse until the quasi-stationary state is reached is called swelling time. At steady state, the dissolution rate is constant and can be defined equally by either the velocity of the retracting front of the polymer or the velocity of the front separating the pure penetrate and the liquid dissolving sublayer. Thus, both fronts are synchronized.

When the dissolution rate equals the penetration rate (i.e. the diffusion rate) a constant thickness surface layer should be observed. The dissolving layer evolution during water conditioning should reflect the different dissolution characteristics of the materials employed. The surface layer thickness is measured as a function of time.

In order to measure the diffusion rates of water, samples may be prepared in the form of plugs fitting to the sample holder (e.g. 2 mm, 4 mm, 6 mm, 7.5 mm and 12 mm long and preferable with the same shape and volume as the desired dosage unit). The sample holder is prepared by translucent glass in a tubular shape and with noticeable marks indicated with a specific distance.

The test proceeds as follows: Place 1 plug incorporated into the glass tube in a vessel—optionally with a water soluble dye (e.g. $Cu^{2+}$)—and the plug/glass tube is placed in a dissolution apparatus e.g. according to monograph: USP 24, page 1941-1950, which is hereby incorporated by reference (see FIG. 1A). By employment of the USP method it is possible to determine the diffusion rate as well as the dissolution rate in the same experiment. The copper ions are blue-coloured so they are visually detectable and due to the metric scale on the tube, the diffusion rate can be calculated (unit is length/time). The dissolution rate is determined by determining the amount of substance (e.g. active substance) released and at the same time determining the length of the matrix composition that has been eroded. Thus, the dissolution rate is also in length/time units. As the dissolution profile easily can be obtained from the data measured, a simple means for the determination of whether the release follows zero order is to investigate the dissolution profile and see whether linearity is present.

Agitation is provided, and the length of the front of matrix is measured at desired time intervals as a function of time. The measurement may be a simple visual identification of the marks on the glass tube.

When the dissolution rate equals the penetration rate a constant thickness surface layer is observed. The different dissolving layers in different matrices obtained during the water contact, reflect the different dissolution characteristics of the matrix. The thickness of the surface layer as a function of time is then compared. The specific aqueous medium may be selected individually.

Dissolution Test

Dissolution tests were performed in accordance with the USP 24, NF 19, (711) Dissolution, Apparatus 2 equipped with a paddle. The dissolution medium was 0.1 N hydrochloric acid during the first 120 min, which was then substituted with a buffer solution pH 6.8. The volume of the dissolution medium was 1000 ml and the rotation speed of the paddle was 120 rpm during the first 120 min and then 50 rpm. Samples were withdrawn at suitable time intervals and analyzed for content of opioid by means of UV spectrometry at a wavelength of 284 nm.

EXAMPLES

A general method for the preparation of a controlled release composition is described below.

Preparation of the Matrix Composition

An accurate amount of the polymer (i.e. in the examples below: the polyethylene oxide) is loaded into a MTI mixer followed by an accurate amount of the active substance and of the pharmaceutically acceptable excipients(s), if any. The mixing is performed at 2000/1500 rpm and at a time period of from 10 min to 20 min. At the start of the mixing the temperature is about 19° C. and the final temperature of the mixture is about 40-43° C. The mixture is then allowed to cool to room temperature and is ready to be fed into an injection moulding machine.

When TPGS is included in the composition, TPGS and PEO are premixed by adding melted TPGS to PEO followed by mixing.

Preparation of the Coating Composition

The coating composition was prepared by first adding the hydroxymethylcellulose then cetostearyl alcohol, and finally the titanium dioxide to an MTI-Mixer at a temperature about 21° C. After mixing for nearly 9 min at 1000 rpm (I: 0.9 A) the mixer was stopped (temperature about 46° C.) and the adhered material manually incorporated into the mixture. The mixture was left to cool for about 10 minutes. The mixing is then finalized with a short high-speed mix in order to minimize lumps formation. The mixture was then allowed to cool to room temperature, after which it had a suitable consistency for being fed into an injection moulding machine.

Example of Coat Composition

Batch: 58014-01-013

| % | Batch | Material | amount (g) | Weight (g) | step |
|---|---|---|---|---|---|
| 79 | 991207-A | Ethocel | 632 | 632 | 1 |
| 20 | 990426-B | Cetylstearyl Alkohol | 160 | 160.1 | 2 |
| 1 | 97051301 | TiO$_2$ | 8 | 8.0 | 3 |
| 100 | | total | 800 | 800.1 | |

The final dosage units may be prepared according to two different methods.

In one method, the coat and the matrix moulded individually followed by a manually incorporation of the moulded matrix plug into the moulded coat. The moulding machine used is an Arburg Allrounder 220 S 250/60.

In the second method, the coat and matrix are moulded in one process where the coat is moulded in a first step and the matrix is moulded directly into the coat in a second step. The moulding machine used is Arburg Allrounder 420 V 800-60/35.

Examples

Example 1

Preparation of a Morphine Containing Controlled Release Composition According to the Invention A composition (batch No. 01-0112-066) according to the invention was prepared from the following ingredients:

| Matrix | |
|---|---|
| Polyethylene oxide 200.000 | 83.5% w//w |
| Morphine sulfate | 16.5% w/w |

The coating and the matrix were prepared as described above. The composition was 9 mm long and had elliptic formed surfaces.

The composition was subjected to the dissolution test described above. The following results were obtained:

| Time (hours) | % w/w release morphine sulfate from the composition |
|---|---|
| 1 | 19.48 |
| 2 | 33.64 |
| 3 | 44.22 |
| 4 | 55.59 |
| 5 | 70.11 |
| 6 | 80.70 |
| 7 | 91.30 |
| 8 | 96.65 |

The result is also shown in FIG. 2 and the release corresponds to a zero order release.

Example 2

Preparation of Morphine-Containing Compositions According to the Invention

In the table below is given details on the composition of 4 different morphine compositions. The content of morphine sulphate in all compositions corresponds to 30 mg morphine sulphate. The volumes of the different compositions were the same, whereas the diameter of the open end surfaces varies.

| No. | Length/mm | Composition (% w/w) | | | | |
|---|---|---|---|---|---|---|
| | | PEO 200.000 | Morphine Sulphate | TPGS | AlO$_2$, 3H$_2$O | Mannitol |
| 1B | 7.5; Ellipse$^a$ | 76.5 | 18.7 | 2.5 | 2.3 | |
| 2B | 12; round$^b$ | 68.7 | 18.7 | 2.6 | | 10.0 |
| 2A | 9; round$^c$ | 69.9 | 17.5 | 2.6 | | 10.0 |
| 1A | 9; round$^d$ | 77.3 | 17.9 | 2.5 | 2.4 | |

$^a$ 150 mm$^3$/20 mm$^2$
$^b$ 137 mm$^3$/diameter 5 mm
$^c$ 150 mm$^3$/16.67 mm$^2$
$^d$ 150 mm$^3$/16.67 mm$^2$ All compositions demonstrated 6 months accelerated stability at 40° C./75% RH and 12 months stability at 25° C./75% RH. In all compositions each single impurity is below 0.1% w/w.

In the following is given the data for the dissolution profiles of each composition:

Composition 2A (See FIG. 3-2A):

| Time/h | % active substance dissolved | |
|---|---|---|
| 0.0 | −0.36 | |
| 1.0 | 23.45 | 20.0 |
| 2.0 | 41.3 | 35.2 |
| 3.0 | 59.5 | 50.7 |
| 4.0 | 75.93 | 64.7 |
| 5.0 | 90.83 | 77.4 |
| 6.0 | 107.34 | 91.5 |
| 6.5 | 113.26 | 96.6 |
| 7.0 | 116.67 | 99.4 |
| 7.5 | 117.24 | 100 |
| 8.0 | 117.28 | 100 |

Figures 1A, 3:
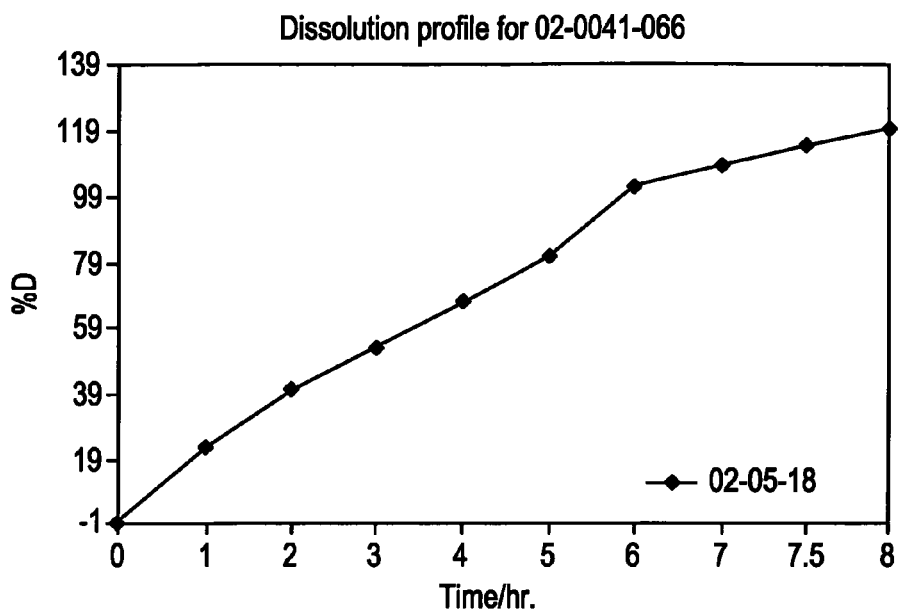
FIG. 3 (1A, 1B, 2A and 2B) shows the dissolution profiles from the compositions of Example 2.
Figures 1B, 3:
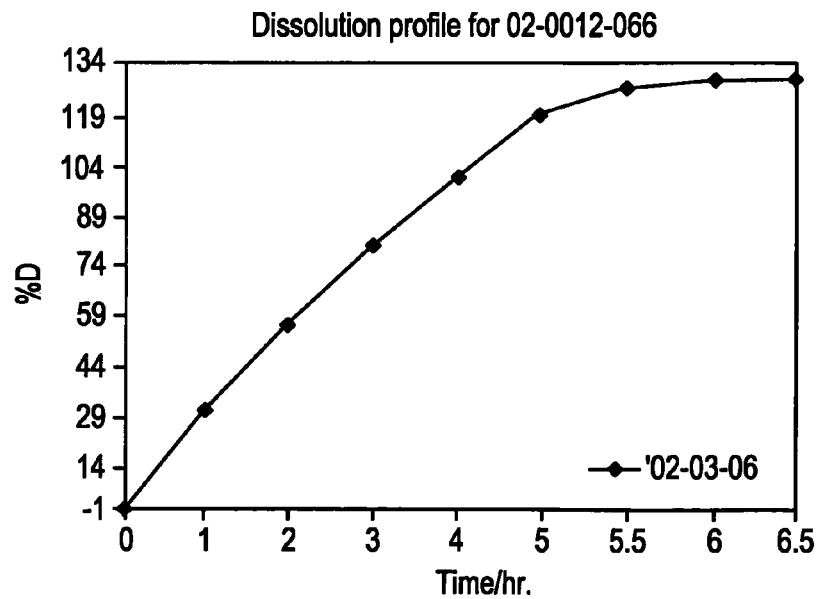
Figures 2A, 3:
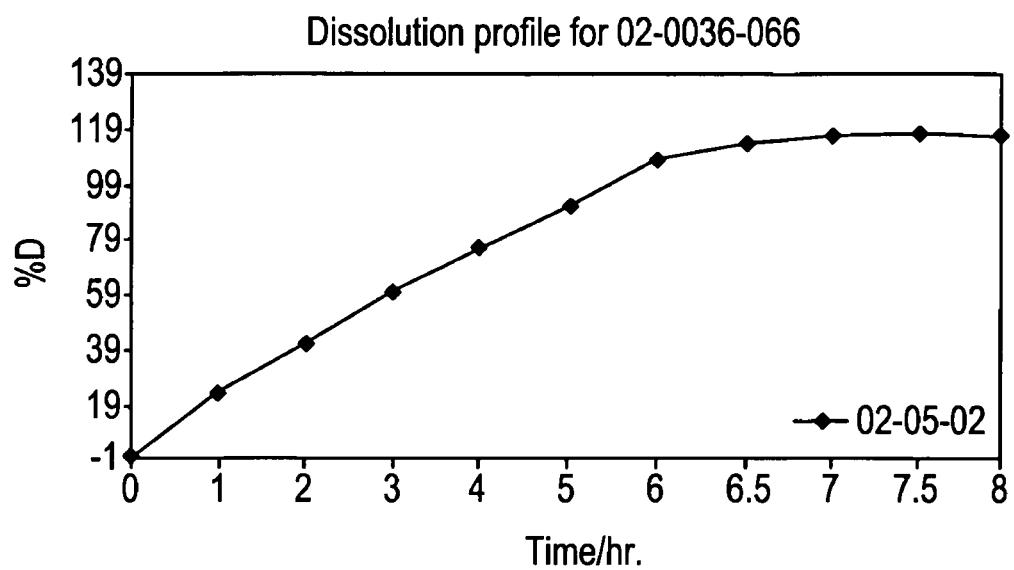
Figures 2B, 3:
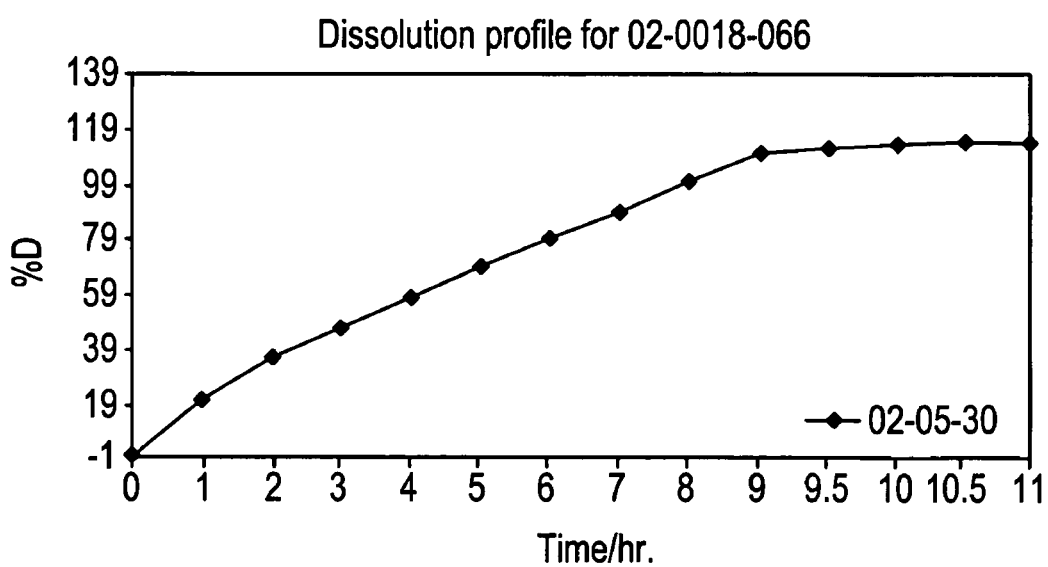

Composition 2B (See FIG. 3-2B)

| Time/h | % active substance dissolved | |
|---|---|---|
| 0.0 | −0.48 | |
| 1.0 | 19.22 | 16.9 |
| 2.0 | 34.44 | 30.0 |
| 3.0 | 44.3 | 39.0 |
| 4.0 | 55.52 | 48.8 |
| 5.0 | 66.13 | 58.2 |
| 6.0 | 76.93 | 67.7 |
| 7.0 | 87.19 | 76.7 |
| 8.0 | 98.11 | 86.3 |
| 9.0 | 109.04 | 96.0 |
| 9.5 | 111.26 | 97.8 |
| 10.0 | 112.63 | 99.1 |
| 10.5 | 113.48 | 100 |
| 11.0 | 113.66 | 100 |

Figure 1B:
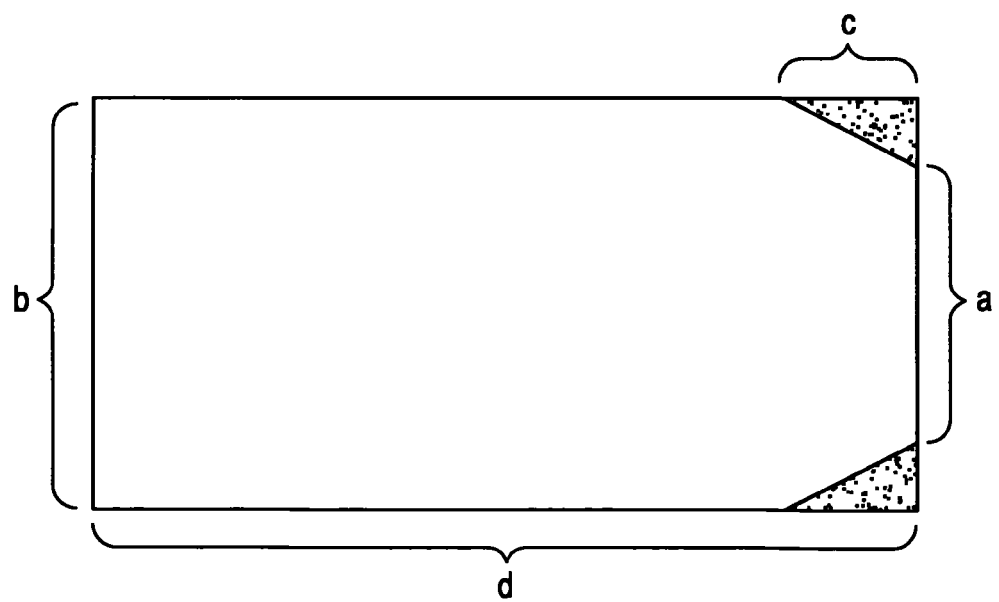
FIG. 1B is a suitable shape for an opioid composition. Suitable values are e.g. a=3 mm, b=4.5 mm, c=1.5 mm and d=9 mm; a=3 mm, b=4.6 mm, c=2 mm and d=9 mm; a=2.3 mm, b=5.3 mm, c=1.5 mm and d=7.5 mm; or a=3.4 mm, b=5.1 mm, c=2 mm and d=7.5 mm

Composition 1B (See FIG. 3-1B)

| Time/h | % active substance dissolved | |
|---|---|---|
| 0.0 | −0.47 | |
| 1.0 | 30.15 | 23.7 |
| 2.0 | 55.72 | 43.9 |
| 3.0 | 77.54 | 61.1 |
| 4.0 | 97.55 | 76.8 |
| 5.0 | 117.57 | 92.6 |
| 5.5 | 124.77 | 98.2 |
| 6.0 | 126.89 | 100 |
| 6.5 | 126.93 | 100 |

Composition 1A (See FIG. 3-1A)

| Time/h | % active substance dissolved | |
|---|---|---|
| 0.0 | −0.423 | |
| 1.0 | 23.17 | 19.3 |
| 2.0 | 40.47 | 33.8 |
| 3.0 | 53.27 | 44.4 |
| 4.0 | 67.13 | 56.0 |
| 5.0 | 80.67 | 67.3 |
| 6.0 | 101.23 | 84.4 |
| 7.0 | 108.16 | 90.2 |
| 7.5 | 114.53 | 95.6 |
| 8.0 | 119.78 | 100 |

The results show that the use of mannitol or aluminiumoxide as a DDA leads to the desired zero order release of morphine sulphate from a composition according to the invention. The above-mentioned compositions were subject to a clinical study. The clinical study is reported in the following example.

Example 3

A Single Dose, Randomized, Cross-Over, Pharmacokinetic Pilot Study on Four Different Morphine Compositions According to the Invention The objectives were to study the pharmacokinetics of morphine after administration of four different morphine compositions according to the invention. The compositions had different shape and size and the DDAs employed in order to enable a zero order dissolution profile were different (mannitol and aluminium oxide, respectively).

16 healthy male volunteers aged 20 to 40 who had given their written informed consent were included in the study.

The volunteers were screened up to three weeks prior to baseline. The first treatment was administered at the baseline visit and second treatment was administered after 2 weeks of wash out. Follow-up visits took place 30 days after the second study period.

The compositions tested were those described in Example 2 above. The dose given corresponds to 30 mg morphine sulphate.

Figure 4:
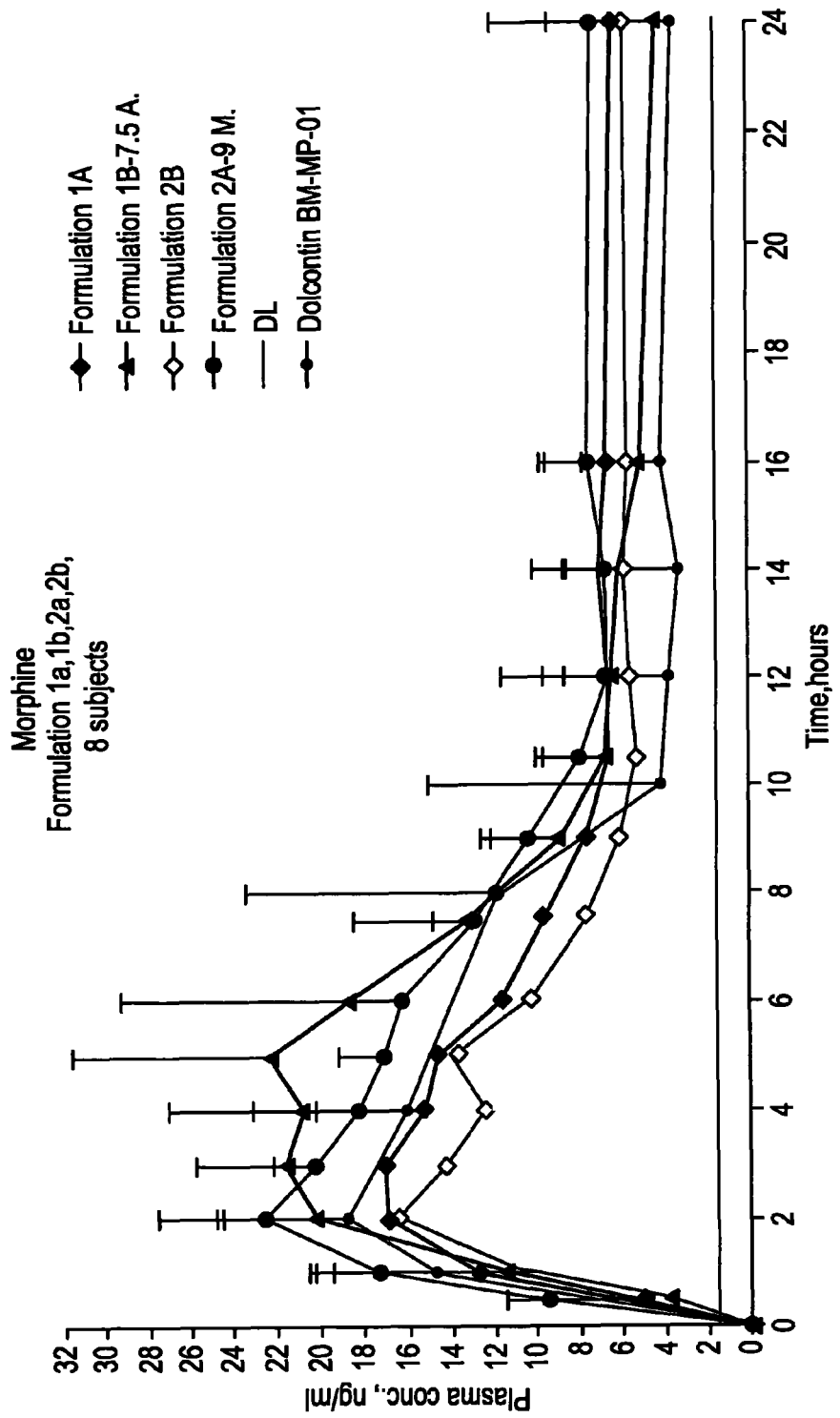
FIG. 4 shows the plasma concentration vs. time profile for the clinical study on healthy volunteers reported in Example 3.

The results of the study are shown in FIG. 4. In FIG. 4 is also included data for a comparative composition, Dolcontin. The results indicate that the shape as well as the size of the composition are important.

Figure 5:
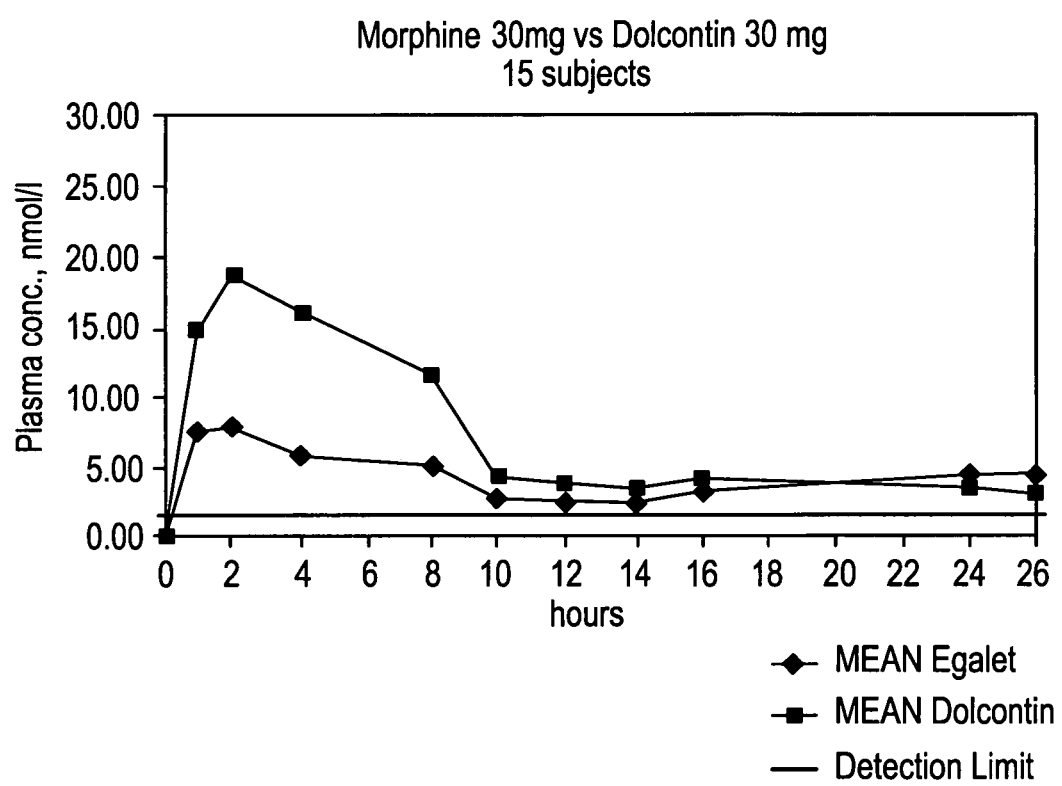
FIG. 5 shows the plasma concentration vs. time profile for the clinical study in phase II reported in Example 3.

Another clinical study has also been performed as a phase II, open, prospective, controlled study in patients with chronic pain. The study included 13 patients with chronic pain for any reason judged by the investigator as stable and in need of opioids analgesics. A composition according to the invention was tested and compared with a commercially available morphine containing composition, Dolcontin. The total morphine sulphate released from the composition according to the invention was about 20 mg (the dosage in Dolcontin was 30 mg). Although there was a difference in the amount administered, it was evident from the study that the therapeutic effect of a composition according to the invention was not different from Dolcontin, i.e. a reduction is the overall dose may be reduced by the use a zero order release composition. Moreover, the adverse effects reported were less compared to the Dolcontin composition, most likely due to the smaller amount of morphine sulphate administered. Another interesting feature is that during the study rescue medication was allowed and there was no difference in the intake of rescue medicine of patients administered with Dolcontin or with a composition according to the invention. FIG. 5 shows the plasma concentration versus time profiles from the study.

The invention claimed is:

1. A pharmaceutical composition for controlled release of at least one therapeutically, prophylactically and/or diagnostically active substance into an aqueous medium by erosion of at least one surface of the composition, the composition comprising:
   a matrix composition comprising:
   a) one or more polyglycol homopolymers having an average molecular weight of from at least about 100,000 daltons to about 700,000 daltons,
   b) an opiod active substance, and, optionally,
   c) one or more pharmaceutically acceptable excipients,
   with the proviso that the matrix composition does not contain a water dispersible or water soluble surface active agent that has at least one domain which is compatible with the polymer in the matrix composition and at least one other domain which is lipophilic, and which has a melting point that is lower than the polymer in the matrix,
   the matrix having a coating having at least one opening exposing at least one surface of said matrix, the coating being insoluble in and impermeable to body fluids and comprising a polymer, wherein any matrix surface exposed to the aqueous medium erodes at a substantially constant rate, so that a zero order release is obtained of at least about 60% w/w of the active substance from the pharmaceutical composition when subject to an in vitro dissolution test according to USP 24, NF 19, 711 Dissolution, employing Apparatus 2 equipped with a paddle,
   the composition having a cylindrical shape optionally with one or more tapered ends.

2. A composition according to claim 1, wherein the opioid is selected from the group consisting of alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene, sufentanil, tilidine, tramadol, pharmaceutically acceptable salts thereof, and mixtures thereof.

3. A composition according to claim 2, wherein the opioid is morphine, morphine 6-glucuronide, morphine 3-glucuronide, dihydromorphine, hydrocodone, hydromorphone, oxycodone, oxymorphone or mixtures thereof.

4. A composition according to claim 1, wherein the release of the opioid from the composition is zero order and about 50% w/w opioid is released from the composition within 3-5 hours as measured by the dissolution test described in claim 1.

5. A composition according to claim 1, wherein the release of the opioid from the composition is zero order and about 75% w/w opioid is released from the composition within 3-12 hours as measured by the dissolution test described in claim 1.

6. A composition according to claim 1, wherein the polyglycol homopolymer comprises a polyethylene oxide.

7. A composition according to claim 1, wherein the matrix composition further comprises a block copolymer of ethylene oxide and propylene oxide that is comprised of up to about 30% w/w of the propylene oxide based block, and has an average molecular weight of from about 8,000 to about 15,000 daltons.

8. A composition according to claim 1, wherein the opioid has a water-solubility of at least 3 mg/ml.

9. A composition according to claim 1, wherein the matrix composition comprises a pharmaceutically acceptable excipient having a water-solubility of at the most 3 mg/ml.

10. A composition according to claim 1, wherein the matrix composition comprises a pharmaceutically acceptable excipient selected from the group consisting of cellulose, microcrystalline cellulose, methyl cellulose, ethyl cellulose, ethylhydroxyethyl cellulose, ethylmethylcellulose, hydroxyethylcellulose, hydroxyethylmethyl cellulose, carboxymethyl cellulose, hydroxypropyl cellulose, hydroxymethylpropyl cellulose, hydroxypropylmethyl cellulose, amylopectin, pectin, starch, sodium starch, kaolin, bentonit, acacia, alginic acid, sodium alginate, calcium alginate, gelatin, molasses, extract of Irish moss, panwar gum, ghatti gum, mucilage of isapol husk, veegum, glycollate, magnesium stearate, calcium stearate, stearic acid, talc, titanium dioxide, silicium dioxide, clays, croscarmellose, gums, and agar.

11. A composition according to claim 1, wherein the opioid has a water-solubility of at the most 3 mg/ml.

12. A composition according to claim 11, wherein the matrix composition comprises a pharmaceutically acceptable excipient having a water-solubility of at least 1 mg/ml.

13. A composition according to claim 1, wherein the matrix composition comprises a pharmaceutically acceptable excipient having a water-solubility of at least about 10 mg/ml in water at ambient temperature.

14. A composition according claim 1, wherein the pharmaceutically acceptable excipient is selected from the group consisting of inorganic acids, inorganic bases, inorganic salts, organic acids or bases and pharmaceutically acceptable salts thereof, monosaccharides, disaccharides, oligosaccharides, and polysaccharides.

15. A composition according to claim 1, wherein the pharmaceutically acceptable excipient is selected from the group consisting of inorganic or organic acids and pharmaceutically acceptable salts thereof.

16. A composition according to claim 15, wherein the organic acid is selected from the group consisting of acetic acid, ethanoic acid, succinic acid, citric acid, tartaric acid, acrylic acid, benzoic acid, malic acid, maleic acid, adipic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, pimelic acid, pyruvic acid, aspartic acid, and glutamic acid.

17. A composition according to claim 16, wherein the organic acid is selected from the group consisting of acetic acid, succinic acid, citric acid, tartaric acid, acrylic acid, benzoic acid, malic acid, maleic acid, and sorbic acid.

18. A composition according to claim 14, wherein the inorganic acid is pyrophosphoric acid, glycerophosphoric acid, ortho phosphoric acid, meta phosphoric acid, boric acid, hydrochloric acid, or sulfuric acid.

19. A composition according to claim 18, wherein the inorganic acid is ortho phosphoric acid or meta phosphoric acid.

20. A composition according to claim 14, wherein the organic bases are selected from the group consisting of p-nitrophenol, succinimide, benzenesulfonamide, 2-hydroxy-2-cyclohexenone, imidazole, pyrrole, diethanolamine, ethyleneamine, tris(hydroxymethyl)aminomethane, hydroxylamine, sodium citrate, aniline, and hydrazine.

21. A composition according to claim 14, wherein the inorganic bases are selected from the group consisting of aluminium oxide, aluminium oxide trihydrate, alumina, sodium hydroxide, potassium hydroxide, calcium carbonate, ammonium carbonate, and ammonium hydroxide.

22. A composition according to claim 14, wherein the pharmaceutically acceptable salt of an organic or inorganic acid is selected from the group consisting of sodium phosphate, sodium dihydrogenphosphate, disodium hydrogenphosphate, potassium phosphate, potassium dihydrogenphosphate, potassium hydrogenphosphate, dicalcium phosphate, sodium sulfate, potassium sulfate, calcium sulfate, sodium carbonate, sodium hydrogencarbonate, potassium carbonate, potassium hydrogencarbonate, calcium carbonate, magnesium carbonate, sodium acetate, potassium acetate, calcium acetate, sodium succinate, potassium succinate, calcium succinate, sodium citrate, potassium citrate, calcium citrate, sodium tartrate, potassium tartrate, calcium tartrate, and zinc sulphate.

23. A composition according to claim 22, wherein the inorganic salt is selected from the group consisting of sodium chloride, potassium chloride, calcium chloride, or magnesium chloride.

24. A composition according to claim 14, wherein the pharmaceutically acceptable excipient is selected from glucose, ribose, arabinose, xylose, lyxose, allose, altrose, inositol, sorbitol, mannose, gulose, idose, galactose, talose, mannitol, fructose, lactose, sucrose, dextrin, dextran, amylose, xylan, and dextrose.

25. A composition according to claim 14, wherein the pharmaceutically acceptable excipient is selected from mannitol, xylitol, sorbitol, sucrose and inositol.

26. A composition according to claim 1, wherein the active substance is present in the matrix composition in a concentration of from about 0.1 to about 98% w/w.

27. A composition according to claim 1, wherein the active substance is present in the matrix composition in a concentration of at the most about 65% w/w.

28. A composition according to claim 1, wherein the active substance is a pharmaceutically active powder.

29. A composition according to claim 28, wherein the powder has a particle size of from about 0.1 μm to about 500 μm.

30. A composition according to claim 1, wherein the polymer in the coating is selected from the group consisting of ethylcellulose, cellulose acetate, cellulose propionate, cellulose nitrate, polyamide, polyethylene, polyethylene terephthalate, polypropylene, polyurethane, polyvinyl acetate, polyvinyl chloride, silicone rubber, latex, polyhydroxybutyrate, polyhydroxyvalerate, teflon, polylactic acid or polyglycolic acid and copolymers thereof, ethylene vinyl acetate, styrene-butadienstyrene and styrene-isoprene styrene.

31. A composition according to claim 1, wherein the coating does not completely crumble or erode before the matrix has completely eroded.

32. A composition according to claim 1, wherein the matrix composition does not contain polyethylene glycol 2000 monostearate or polyethylene glycol 400 monostearate.

33. A composition according to claim 1 comprising one or more antioxidants.

34. A composition according to claim 1 further comprising a second pharmaceutically acceptable excipient selected from the group consisting of fillers, diluents, disintegrants, glidants, pH-adjusting agents, viscosity adjusting agents, solubility increasing or decreasing agents, osmotically active agents and solvents.

35. A composition according to claim 1, wherein the matrix composition further comprises a block copolymer of ethylene oxide and propylene oxide having an average molecular weight of from about 5,000 to about 30,000 daltons.

36. A composition according to claim 1, wherein the matrix composition further comprises a polymer selected from the group consisting of poly(ethylene-glycol-b-(DL-lactic acid-co-glycolic acid)-b-ethylene glycol (PEG-PLGA PEG), poly((DL-lactic acid-co-glycolic acid)-g-ethylene glycol) (PLGA-g-PEG), and polyethylene oxide-polypropylene oxide (PEO-PPO).

37. A composition according to claim 1, wherein the opening of the coating exposes a surface at an end of the cylindrically shaped matrix, the opening having an area equivalent to the volume of the cylindrically shaped matrix divided by the length of the cylindrically shaped matrix.

38. A composition according to claim 1, consisting of said matrix composition having said coating.

* * * * *